(12) United States Patent
Smail et al.

(10) Patent No.: US 10,532,880 B2
(45) Date of Patent: Jan. 14, 2020

(54) AEROSOL DEVICE FOR HAIR SHAPING AND/OR STYLE RETENTION

(71) Applicant: L'OREAL, Paris (FR)

(72) Inventors: Nadia Smail, Vernouillet (FR); Lionel Aubert, Asnieres sur Oise (FR); Jonathan Gawtrey, Boulogne (FR); Nicolas Albisetti, Saint Gratien (FR)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 15/541,738

(22) PCT Filed: Jan. 8, 2016

(86) PCT No.: PCT/EP2016/050295
§ 371 (c)(1),
(2) Date: Jul. 6, 2017

(87) PCT Pub. No.: WO2016/110575
PCT Pub. Date: Jul. 14, 2016

(65) Prior Publication Data
US 2018/0016087 A1    Jan. 18, 2018

(30) Foreign Application Priority Data
Jan. 8, 2015 (FR) ..................... 15 50161

(51) Int. Cl.
*A61Q 5/06* (2006.01)
*A61K 8/81* (2006.01)
(Continued)

(52) U.S. Cl.
CPC ............. *B65D 83/30* (2013.01); *A45D 34/04* (2013.01); *A61K 8/046* (2013.01); *A61K 8/19* (2013.01);
(Continued)

(58) Field of Classification Search
None
See application file for complete search history.

(56) References Cited

U.S. PATENT DOCUMENTS 2,047,398 A    7/1936  Voss et al.
2,102,113 A    12/1937  Djordjevitch
(Continued)

FOREIGN PATENT DOCUMENTS

DE           2330956 A1    1/1974
DE    10 2005 025 016 A1    12/2005
(Continued)

OTHER PUBLICATIONS

Brunauer et al., "Adsorption of Gases in Multimolecular Layers," Journal of the American Chemical Society, vol. 60, Feb. 1938, pp. 309-319.
(Continued)

*Primary Examiner* — Aradhana Sasan
(74) *Attorney, Agent, or Firm* — The Marbury Law Group, PLLC

(57) ABSTRACT

The invention relates to an aerosol device comprising:
a container containing:
  one or more propellants, and
  a composition comprising one or more fixing polymers and/or one or more styling powder(s) comprising one or more water-insoluble inorganic compounds,
it being possible for the propellant(s) to be present in the composition or, in the container, separate from the composition,
a means for dispensing said composition comprising:
  a body (3) that is open at its two opposite axial ends,
  an engaging part (10) that is open at its two opposite axial ends, at least partially defining at least one dispensing orifice (12).

20 Claims, 6 Drawing Sheets

(51) Int. Cl.

| | | |
|---|---|---|
| *A61K 8/04* | (2006.01) | |
| *A61K 8/19* | (2006.01) | |
| *A61K 8/31* | (2006.01) | |
| *A61K 8/34* | (2006.01) | |
| *A61K 8/41* | (2006.01) | |
| *A61K 8/60* | (2006.01) | |
| *A61K 8/891* | (2006.01) | |
| *A61K 8/892* | (2006.01) | |
| *B65D 83/14* | (2006.01) | |
| *B65D 83/30* | (2006.01) | |
| *A45D 34/04* | (2006.01) | |
| *A45D 34/00* | (2006.01) | |

(52) U.S. Cl.
CPC ............... *A61K 8/31* (2013.01); *A61K 8/34* (2013.01); *A61K 8/41* (2013.01); *A61K 8/60* (2013.01); *A61K 8/817* (2013.01); *A61K 8/8147* (2013.01); *A61K 8/891* (2013.01); *A61K 8/892* (2013.01); *A61Q 5/06* (2013.01); *B65D 83/752* (2013.01); *A45D 2034/007* (2013.01); *A45D 2200/057* (2013.01); *A61K 2800/87* (2013.01)

(56) References Cited

U.S. PATENT DOCUMENTS

| | | |
|---|---|---|
| 2,723,248 A | 11/1955 | Wright |
| 3,161,460 A | 12/1964 | Huber |
| 3,504,862 A | 4/1970 | Lowry |
| 3,579,629 A | 5/1971 | Pasero et al. |
| 3,589,978 A | 6/1971 | Kamal et al. |
| 3,628,733 A | 12/1971 | Kahn |
| 3,716,633 A | 2/1973 | Viout et al. |
| 3,767,125 A | 10/1973 | Gehres et al. |
| 3,792,068 A | 2/1974 | Luedders et al. |
| 3,810,977 A | 5/1974 | Levine et al. |
| 3,836,537 A | 9/1974 | Boerwinkle et al. |
| 3,910,862 A | 10/1975 | Barabas et al. |
| 3,925,542 A | 12/1975 | Viout et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,031,307 A | 6/1977 | DeMartino et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,165,367 A | 8/1979 | Chakrabarti |
| 4,223,009 A | 9/1980 | Chakrabarti |
| 4,282,203 A | 8/1981 | Jacquet et al. |
| 4,289,752 A | 9/1981 | Mahieu et al. |
| 4,401,271 A | 8/1983 | Hansen |
| 4,450,151 A | 5/1984 | Shinozawa |
| 4,557,916 A | 12/1985 | Withiam |
| 4,605,553 A | 8/1986 | Passalacqua |
| 4,693,925 A | 9/1987 | Cheung et al. |
| 4,728,571 A | 3/1988 | Clemens et al. |
| 4,822,596 A | 4/1989 | Callingham et al. |
| 4,871,529 A | 10/1989 | Sramek |
| 4,874,554 A | 10/1989 | Lange et al. |
| 4,957,732 A | 9/1990 | Grollier et al. |
| 4,972,037 A | 11/1990 | Garbe et al. |
| 4,983,377 A | 1/1991 | Murphy et al. |
| 5,297,739 A | 3/1994 | Allen |
| 5,300,284 A | 4/1994 | Wiechers et al. |
| 5,508,259 A | 4/1996 | Holzner et al. |
| 5,538,717 A | 7/1996 | La Poterie |
| 5,614,173 A | 3/1997 | Ulmer et al. |
| 5,643,557 A * | 7/1997 | Eteve ............... A61K 8/0241 424/59 |
| 5,879,669 A | 3/1999 | Clausen et al. |
| 6,106,813 A | 8/2000 | Mondet et al. |
| 6,166,093 A | 12/2000 | Mougin et al. |
| 6,210,689 B1 | 4/2001 | Martino et al. |
| 6,245,324 B1 | 6/2001 | Hough et al. |
| 6,319,959 B1 | 11/2001 | Mougin et al. |
| 6,350,434 B1 | 2/2002 | Bhatt et al. |
| 6,372,876 B1 | 4/2002 | Kim et al. |
| 6,395,265 B1 | 5/2002 | Mougin et al. |
| 6,592,854 B1 | 7/2003 | Dupuis |
| 6,751,886 B2 * | 6/2004 | Chang ............... A45D 20/122 34/96 |
| 7,063,834 B2 | 6/2006 | Mougin et al. |
| 7,585,824 B2 | 9/2009 | Popplewell et al. |
| 2002/0031478 A1 | 3/2002 | Keller et al. |
| 2002/0150546 A1 | 10/2002 | Mougin et al. |
| 2003/0163878 A1 | 9/2003 | Pruche |
| 2003/0185777 A1 | 10/2003 | Banowski et al. |
| 2003/0191271 A1 | 10/2003 | Mondet et al. |
| 2004/0047812 A1 | 3/2004 | Pataut et al. |
| 2004/0170575 A1 | 9/2004 | Belli et al. |
| 2004/0175404 A1 | 9/2004 | Shefer et al. |
| 2005/0163737 A1 | 7/2005 | Lemoine et al. |
| 2005/0220723 A1 | 10/2005 | Benabdillah et al. |
| 2008/0019928 A1 | 1/2008 | Franzke et al. |
| 2008/0172807 A1 | 7/2008 | Brun |
| 2008/0274071 A1 | 11/2008 | Kaplan et al. |
| 2009/0061004 A1 | 3/2009 | Birkel et al. |
| 2010/0040572 A1 | 2/2010 | Mougin |
| 2012/0097180 A1 | 4/2012 | Harris et al. |
| 2012/0171264 A1 | 7/2012 | Bernet et al. |
| 2012/0282190 A1 | 11/2012 | Hammer |
| 2013/0289080 A1 | 10/2013 | Masse et al. |
| 2013/0340786 A1 * | 12/2013 | Rodrigues ............... A61K 8/046 132/210 |
| 2014/0030196 A1 | 1/2014 | Russell et al. |
| 2014/0079747 A1 | 3/2014 | Dihora et al. |
| 2015/0014443 A1 | 1/2015 | Albisetti |
| 2015/0041559 A1 | 2/2015 | Albisetti |
| 2015/0104397 A1 | 4/2015 | Smail et al. |
| 2015/0139917 A1 | 5/2015 | Gawtrey et al. |
| 2016/0106634 A1 | 4/2016 | Gawtrey et al. |
| 2018/0016087 A1 | 1/2018 | Smail et al. |

FOREIGN PATENT DOCUMENTS

| | | |
|---|---|---|
| DE | 102008035013 A1 | 1/2010 |
| EP | 0080976 A1 | 6/1983 |
| EP | 0095238 A2 | 11/1983 |
| EP | 0186507 A2 | 7/1986 |
| EP | 0342834 A2 | 11/1989 |
| EP | 0412704 A2 | 2/1991 |
| EP | 0412707 A1 | 2/1991 |
| EP | 0530974 A1 | 3/1993 |
| EP | 0582152 A2 | 2/1994 |
| EP | 0619111 A1 | 10/1994 |
| EP | 0637600 A1 | 2/1995 |
| EP | 0648485 A1 | 4/1995 |
| EP | 0751162 A1 | 1/1997 |
| EP | 0 974 332 A1 | 1/2000 |
| EP | 1026220 A1 | 8/2000 |
| EP | 1407754 A1 | 4/2004 |
| EP | 2444160 A1 | 4/2012 |
| EP | 2777770 A1 | 9/2014 |
| FR | 1222944 A | 6/1960 |
| FR | 1400366 A | 5/1965 |
| FR | 1564110 A | 3/1968 |
| FR | 1578989 A | 8/1969 |
| FR | 1580545 A | 9/1969 |
| FR | 1600138 A | 7/1970 |
| FR | 2077143 A | 10/1971 |
| FR | 2198719 A1 | 4/1974 |
| FR | 2265781 A1 | 10/1975 |
| FR | 2265782 A1 | 10/1975 |
| FR | 2350384 A1 | 12/1977 |
| FR | 2357241 A2 | 2/1978 |
| FR | 2393573 A1 | 1/1979 |
| FR | 2434194 A1 | 3/1980 |
| FR | 2439798 A1 | 5/1980 |
| FR | 2589476 A1 | 5/1987 |
| FR | 2715841 A1 | 8/1995 |

(56) References Cited

FOREIGN PATENT DOCUMENTS

| | | |
|---|---|---|
| FR | 2743297 A1 | 7/1997 |
| FR | 2814943 A1 | 4/2002 |
| FR | 2924341 A1 | 6/2009 |
| FR | 2980125 A1 | 3/2013 |
| FR | 2985201 A1 | 7/2013 |
| FR | 2985202 A1 | 7/2013 |
| FR | 2990131 A1 | 11/2013 |
| FR | 2990133 A1 | 11/2013 |
| FR | 3004929 A1 | 10/2014 |
| GB | 839805 A | 6/1960 |
| GB | 922457 A | 4/1963 |
| GB | 1021400 A | 3/1966 |
| GB | 1218222 A | 1/1971 |
| GB | 1235908 A | 6/1971 |
| GB | 1331819 A | 9/1973 |
| GB | 1408388 A | 10/1975 |
| GB | 1572626 A | 7/1980 |
| JP | 2011-213619 A | 10/2011 |
| LU | 75370 A1 | 2/1978 |
| LU | 75371 A1 | 2/1978 |
| WO | 93/23009 A1 | 11/1993 |
| WO | 94/03510 A1 | 2/1994 |
| WO | 95/00578 A1 | 1/1995 |
| WO | 98/43599 A1 | 10/1998 |
| WO | 02/078653 A1 | 10/2002 |
| WO | 02/096379 A1 | 12/2002 |
| WO | 03/049711 A2 | 6/2003 |
| WO | 2004/043608 A1 | 5/2004 |
| WO | 2011/019539 A2 | 2/2011 |
| WO | 2011/056625 A1 | 5/2011 |
| WO | 2012/035053 A1 | 3/2012 |
| WO | 2012/080255 A2 | 6/2012 |
| WO | 2013/064918 A1 | 5/2013 |
| WO | 2013/167530 A2 | 11/2013 |
| WO | 2013/167536 A2 | 11/2013 |
| WO | 2014/177646 A2 | 11/2014 |
| WO | 2014/177647 A1 | 11/2014 |
| WO | 2014/177649 A1 | 11/2014 |
| WO | 2016/001190 A1 | 1/2016 |
| WO | 2016/005703 A1 | 1/2016 |
| WO | 2016/066729 A1 | 5/2016 |
| WO | 2016/066730 A1 | 5/2016 |
| WO | 2016/110578 A1 | 7/2016 |
| WO | 2016/110579 A1 | 7/2016 |

OTHER PUBLICATIONS

International Search Report for PCT/EP2016/050295, dated Mar. 23, 2016.
International Search Report for PCT/EP2016/050299, dated Mar. 23, 2016.
International Search Report for PCT/EP2016/050300, dated Mar. 16, 2016.
Final Office Action for copending U.S. Appl. No. 15/324,804, dated Nov. 30, 2018.
Non-Final Office Action for copending U.S. Appl. No. 14/399,764, dated Dec. 5, 2018.
Non-Final Office Action for copending U.S. Appl. No. 15/523,242, dated Dec. 17, 2018.
International Search Report for counterpart PCT/EP2013/059382, dated Jun. 20, 2014.
International Search Report for counterpart PCT/EP2013/059393, dated Jun. 20, 2014.
Bezard et al., "Triglycerides of Coconut Oil," Journal of American Oil Society, 48, Mar. 3, 1971, pp. 134-139.
Oscar Blandi, http://www.skinstore.com/p-6885-oscar-blandi-pronto-dry-shampoo-spray.aspx. Published Jun. 13, 2011.
Database WPI Week 201172, Thomas Scientific, London, GB, AN 2011-N36295, XP002690571 (Jan. 25, 2013).
Mintel: "72h Anti-Perspirant Deodorant," XP007923192, Jan. 2014.
Mintel: "Brown Hair Powder Shampoo," Jun. 2011.
Mintel: "Code 10 Hair Styling Cream," XP007923186, Sep. 2001.
Mintel: "Dry Shampoo," XP007923191, Jan. 2014.
Mintel: "Foot Deodorant Spray," XP007923193, Oct. 2013.
Mintel: "One More Day Dry Shampoo," XP007923187, Aug. 2013.
Mintel: "Refresh Dry Shampoo," Apr. 2010.
Oxford Dictionary, Half-Ester, http://www.oxfordreference.com/view/10.1093/acref/9780198529170.001.0001/acref-9780198529170-e-8589, retrieved online on Oct. 19, 2017 (Year:2017).
Todd, Charles, et al., "Volatile Silicone Fluids for Cosmetic Formulations," Cosmetics and Toiletries, vol. 91, Jan. 1976, pp. 29-32.
Non-Final Office Action for copending U.S. Appl. No. 14/399,753, dated Sep. 8, 2015.
Final Office Action for copending U.S. Appl. No. 14/399,753, dated Mar. 30, 2016.
Non-Final Office Action for copending U.S. Appl. No. 14/399,764, dated Dec. 17, 2015.
International Search Report for counterpart PCT/EP2014/058896, dated Sep. 23, 2014.
International Search Report and Written Opinion for counterpart PCT/EP2014/058892, dated Oct. 29, 2014.
International Search Report for counterpart PCT/EP2014/058894, dated Sep. 29, 2014.
Final Office Action for copending U.S. Appl. No. 13/993,413, dated Nov. 14, 2016.
Final Office Action for copending U.S. Appl. No. 14/399,764, dated Aug. 5, 2016.
Non-Final Office Action for copending U.S. Appl. No. 14/888,002, dated Sep. 9, 2016.
Non-Final Office Action for copending U.S. Appl. No. 14/787,983, dated Sep. 15, 2016.
Final Office Action for copending U.S. Appl. No. 14/399,753, dated Sep. 30, 2016.
Non-Final Office Action for copending U.S. Appl. No. 14/888,013, dated Apr. 13, 2017.
Non-Final Office Action for copending U.S. Appl. No. 14/399,764, dated Mar. 8, 2017.
International Search Report for counterpart PCT/FR2015/051896, dated Oct. 19, 2015.
International Search Report for counterpart PCT/EP2015/075061, dated Jan. 20, 2016.
International Search Report for counterpart PCT/EP2015/075062, dated Jan. 26, 2016.
Non-Final Office Action for copending U.S. Appl. No. 15/324,804, dated Mar. 5, 2018.
Non-Final Office Action for copending U.S. Appl. No. 15/523,232, dated Feb. 23, 2018.
Non-Final Office Action for copending U.S. Appl. No. 15/523,242, dated Aug. 31, 2017.
Final Office Action for copending U.S. Appl. No. 14/888,013, dated Aug. 15, 2017.
Final Office Action for copending U.S. Appl. No. 14/888,002, dated Sep. 21, 2017.
Final Office Action for copending U.S. Appl. No. 14/399,764, dated Aug. 16, 2017.
Non-Final Office Action for copending U.S. Appl. No. 14/399,753, dated Oct. 4, 2017.
Non-Final Office Action for copending U.S. Appl. No. 14/787,983, dated May 11, 2018.
Non-Final Office Action for copending U.S. Appl. No. 15/523,242, dated Mar. 27, 2018.
International Search Report for counterpart Application PCT/EP2011/072617, dated Jul. 5, 2012.
Non-Final Office Action for copending U.S. Appl. No. 13/993,413, dated May 19, 2015.
Final Office Action for copending U.S. Appl. No. 13/993,413, dated Dec. 30, 2015.
Non-Final Office Action for copending U.S. Appl. No. 13/993,413, dated Nov. 8, 2017.
Final Office Action for copending U.S. Appl. No. 13/993,413, dated Jul. 5, 2018.
Non-Final Office Action for co-pending U.S. Appl. No. 14/787,983, dated Jun. 26, 2019.
Final Office Action for co-pending U.S. Appl. No. 14/787,983, dated Dec. 27, 2018.

(56) References Cited

OTHER PUBLICATIONS

Final Office Action for co-pending U.S. Appl. No. 15/523,232, dated Jan. 25, 2019.
Non-Final Office Action for co-pending U.S. Appl. No. 15/541,741, dated Feb. 27, 2019.
International Search Report for counterpart Application No. PCT/EP2015/064780, dated Sep. 14, 2015.
Porter, M.R., "Handbook of Surfactants," published by Blackie & Son (Glasgow and London), 1991, pp. 116-178.
Mintel: "Styling Mousse," XP002736036, Nov. 2008.
Non-Final Office Action for co-pending U.S. Appl. No. 14/888,013, dated Mar. 14, 2019.
Final Office Action for co-pending U.S. Appl. No. 15/541,741, dated Jul. 11, 2019.
Final Office Action for co-pending U.S. Appl. No. 14/399,764, dated Jun. 7, 2019.
Notice of Allowance for co-pending U.S. Appl. No. 15/523,242, dated Jun. 12, 2019.
Mintel: "Clean Freak Refreshing Dry Shampoo," XP007923188, Demert Brands, Mar. 2014.
Non-Final Office Action for co-pending U.S. Appl. No. 14/888,002, dated Oct. 7, 2019.

\* cited by examiner

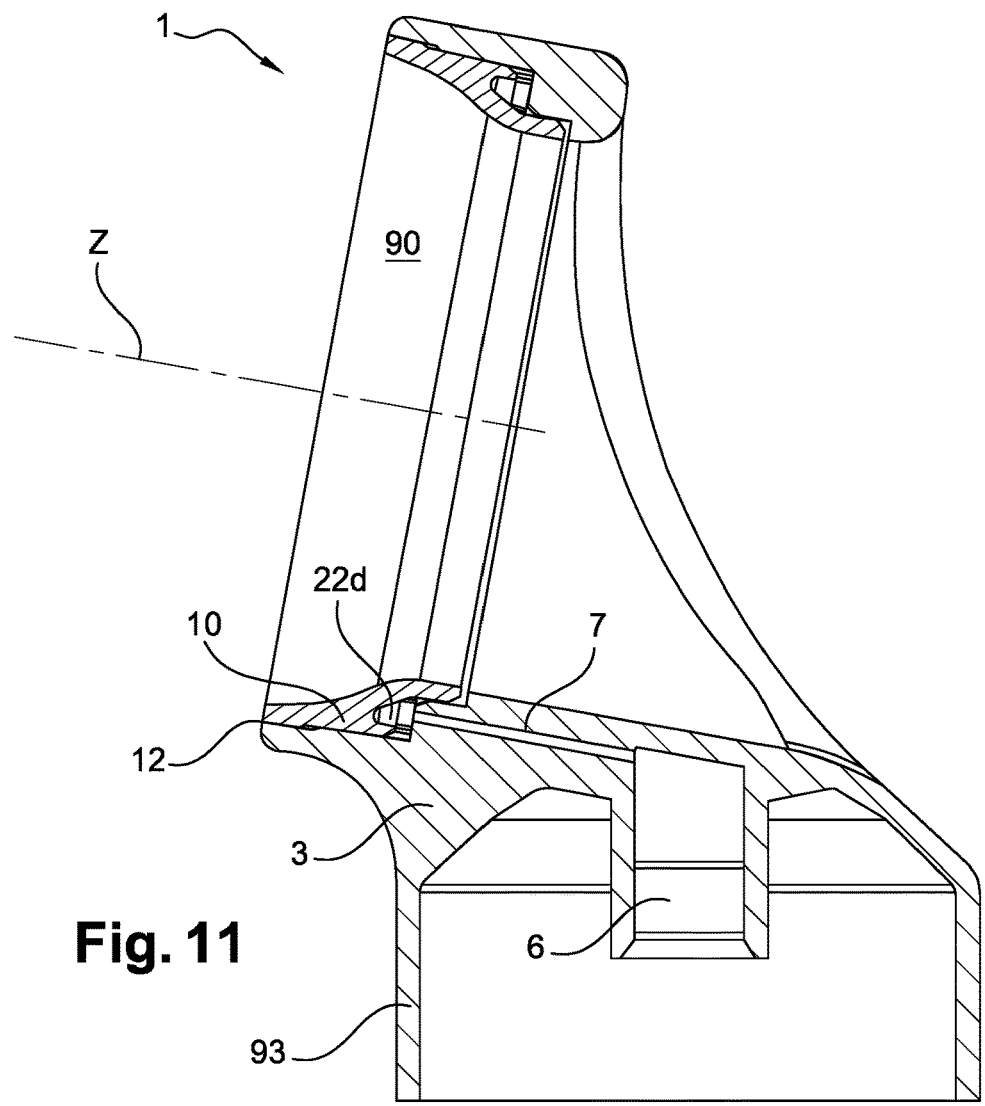
Fig. 11
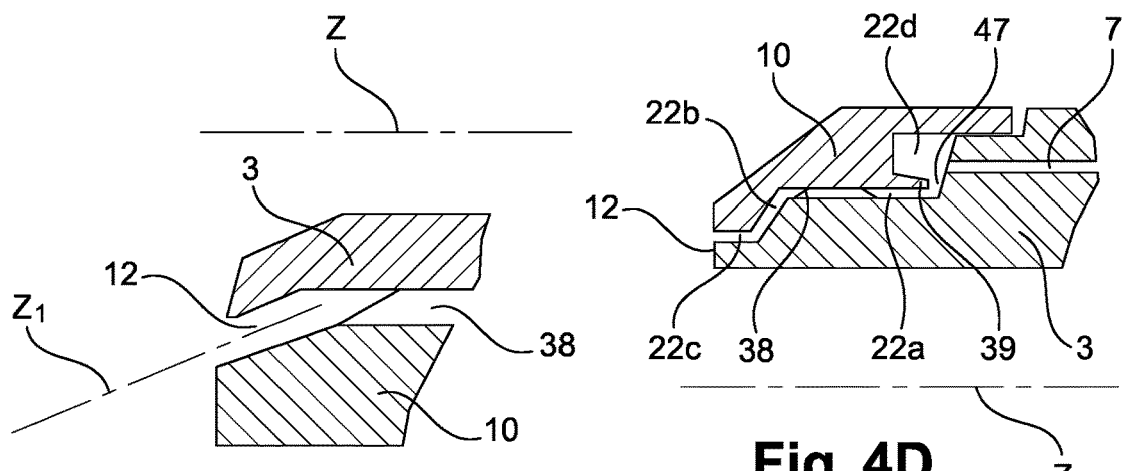
Fig. 4E
Fig. 4D

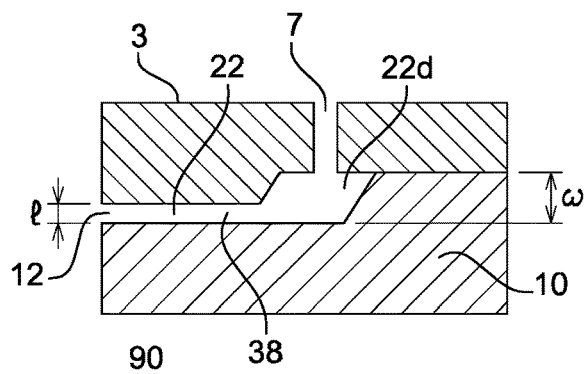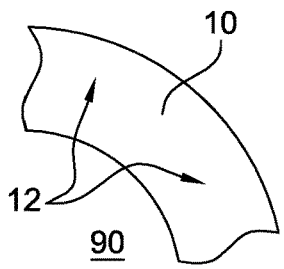
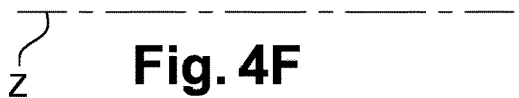
Fig. 4F
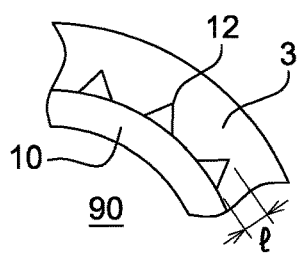
Fig. 8B
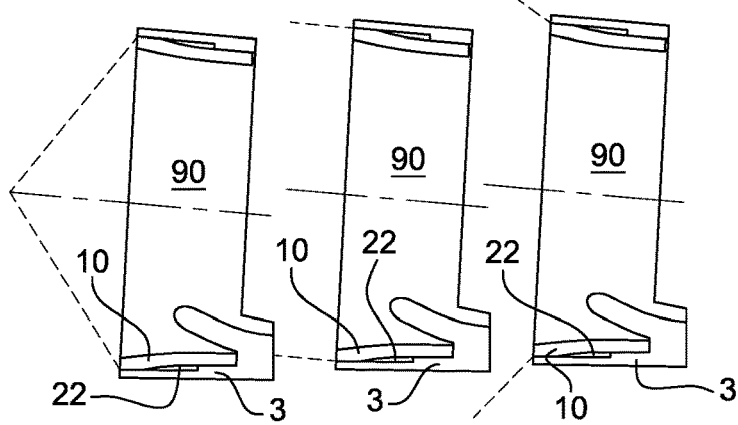
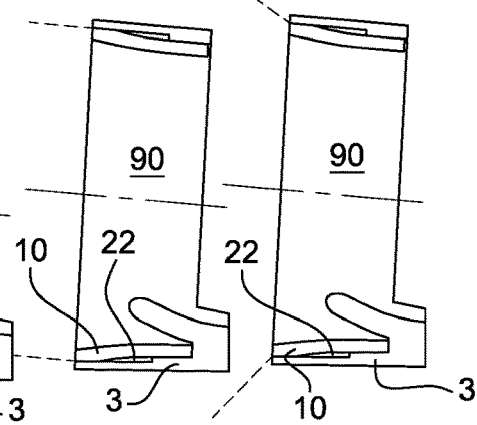
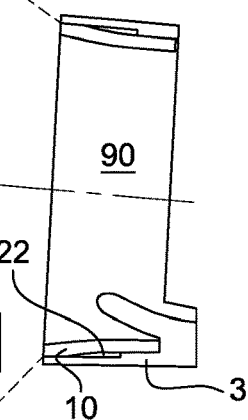
Fig. 10B  Fig. 13A  Fig. 13B  Fig. 13C
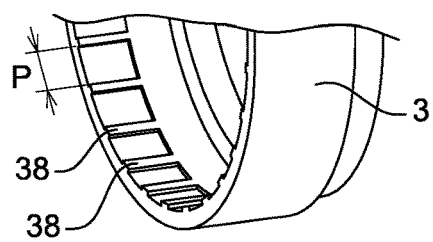
Fig. 12A
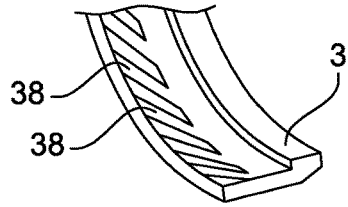
Fig. 12B
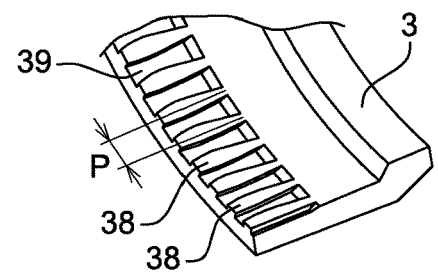
Fig. 12C

AEROSOL DEVICE FOR HAIR SHAPING AND/OR STYLE RETENTION

CROSS REFERENCE TO RELATED APPLICATIONS

This is a national stage application of PCT/EP2016/050295, filed internationally on Jan. 8, 2016, which claims priority to French Application No. 1550161, filed on Jan. 8, 2015, both of which are incorporated by reference herein in their entireties.

The present invention relates to an aerosol device comprising a particular dispensing means and a composition based on at least one fixing polymer and/or on at least one styling powder, comprising at least one water-insoluble inorganic compound, and to a process for treating the hair, particularly for hair shaping and/or for style retention.

The hair products for shaping and/or retaining the hairstyle that are the most widespread on the cosmetics market are spray compositions, such as lacquers and sprays. They are composed essentially of an alcoholic or aqueous solution and of one or more materials, generally polymeric resins, also referred to as fixing components, whose function is to form joins between the individual hairs, in a blend with various cosmetic adjuvants.

These products provide for fixing and for holding of the hairstyle over time. In practice, however, these products are not entirely satisfactory, particularly in terms of hairstyle result. The aerosol sprays conventionally used in fact result in a set hairstyle, which gives a helmet effect, the hairs being stuck together.

There is therefore a need for development of a new aerosol device comprising a hair shaping composition which makes it possible to obtain good fixing of the hairstyle while obtaining a natural look.

The applicant has found, surprisingly and advantageously, that the use of a device equipped with a dispensing means comprising a body that is open at its two opposite axial ends an engaging part that is open at its two opposite axial ends, at least partially defining a dispensing orifice, for dispensing a composition comprising at least one fixing polymer and/or at least one styling powder comprising at least one water-insoluble inorganic compound makes it possible to easily and rapidly obtain a manageable and light hairstyle.

According to a first of its aspects, a subject of the invention is an aerosol device comprising:
  a container containing:
    one or more propellants, and
    a composition comprising one or more fixing polymers and/or one or more styling powder(s) comprising one or more water-insoluble inorganic compounds, it being possible for the propellant(s) to be present in the composition or, in the container, separate from the composition,
  a means for dispensing said composition comprising:
    a body that is open at its two opposite axial ends,
    an engaging part that is open at its two opposite axial ends, at least partially defining at least one dispensing orifice.

This particular combination allows easy application and a uniform, fine, light distribution of the hair composition on the head of hair, thus resulting in shaping of the hairstyle with a natural result.

The composition according to the invention thus allows the hair to be fixed appropriately, leading to satisfactory shaping and/or satisfactory retaining of the style, while conferring in particular manageability, lightness and softness on the head of hair.

The present invention also relates to a process for treating the hair, and in particular for shaping the hair and/or retaining the hairstyle, which comprises the use of the device as described above. In particular, the process for treating the hair comprises a step of applying, to dry or wet hair, a composition sprayed from an aerosol device according to the invention, optionally to be rinsed off after an optional leave-on time or after optional drying.

Other subjects, characteristics, aspects and advantages of the invention will emerge even more clearly on reading the description and the example that follows.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more".

According to the invention, the aerosol device comprises a container which contains a composition comprising one or more fixing polymers and/or one or more styling powder(s) comprising one or more water-insoluble inorganic compounds.

The composition according to the invention may comprise at least one fixing polymer.

Within the context of the invention, the term "fixing polymer" is intended to mean any polymer that is capable, by application to the hair, of giving a shape to the head of hair or of allowing form retention of the hair in an already acquired shape.

The fixing polymer(s) used are chosen from ionic, especially anionic, cationic or amphoteric, and nonionic fixing polymers, and mixtures thereof.

Anionic polymers that may be mentioned include polymers containing groups derived from carboxylic, sulfonic or phosphoric acids, and having a number-average molecular weight of between 500 and 5 000 000.

The carboxylic groups are provided by unsaturated monocarboxylic or dicarboxylic acid monomers, such as those corresponding to the formula:

in which n is an integer from 0 to 10, A denotes a methylene group which is optionally connected to the carbon atom of the unsaturated group or to the neighbouring methylene group when n is greater than 1, via a heteroatom such as oxygen or sulfur, $R_1$ denotes a hydrogen atom or a phenyl or benzyl group, $R_2$ denotes a hydrogen atom, an alkyl group containing from 1 to 4 carbon atoms, or a carboxyl group, $R_3$ denotes a hydrogen atom, an alkyl group containing from 1 to 4 carbon atoms, or a —$CH_2$—COOH, phenyl or benzyl group.

In formula (I) above, the alkyl group containing from 1 to 4 carbon atoms may in particular denote methyl and ethyl groups.

The anionic fixing polymers containing carboxylic or sulfonic groups that are preferred are:

A) Copolymers of acrylic or methacrylic acid or salts thereof, including copolymers of acrylic acid and acrylamide, and methacrylic acid/acrylic acid/ethyl acrylate/methyl methacrylate copolymers, more particularly Amerhold DR 25 sold by the company Amerchol, and sodium salts of polyhydroxycarboxylic acids. Mention may also be made of methacrylic acid/ethyl acrylate copolymers, in particular in aqueous dispersion, such as Luviflex Soft and Luvimer MAE, which are sold by the company BASF.

B) Copolymers of acrylic or methacrylic acids with a monoethylenic monomer such as ethylene, styrene, vinyl esters, acrylic or methacrylic acid esters, which are optionally grafted on a polyalkylene glycol such as polyethylene glycol, and are optionally crosslinked. Such polymers are described in particular in French patent 1 222 944 and German patent application No. 2 330 956, the copolymers of this type comprising an optionally N-alkylated and/or hydroxyalkylated acrylamide unit in their chain as described especially in Luxembourg patent applications 75370 and 75371. Mention may also be made of copolymers of acrylic acid and $C_1$-$C_4$ alkyl methacrylate.

As another anionic fixing polymer from this class, mention may also be made of the branched anionic butyl acrylate/acrylic acid/methacrylic acid block polymer sold under the name Fixate G-100 L by the company Lubrizol (INCI name AMP-Acylates/Allyl Methacrylate Copolymer).

C) Copolymers derived from crotonic acid, such as those comprising, in their chain, vinyl propionate or acetate units, and optionally other monomers such as allyl or methallyl esters, vinyl ether or vinyl ester of a linear or branched, saturated carboxylic acid with a long hydrocarbon-based chain, such as those comprising at least 5 carbon atoms, it being possible for these polymers optionally to be grafted and crosslinked, or else a vinyl, allyl or methallyl ester of an α- or β-cyclic carboxylic acid. Such polymers are described, inter alia, in French patents Nos. 1 222 944, 1 580 545, 2 265 782, 2 265 781, 1 564 110 and 2 439 798. Commercial products that fall within this category are the resins 28-29-30, 26-13-14 and 28-13-10 sold by the company National Starch.

Mention may also be made, as copolymer derived from crotonic acid, of crotonic acid/vinyl acetate/vinyl tert-butylbenzoate terpolymers, and in particular Mexomere PW supplied by the company Chimex.

D) Polymers derived from maleic, fumaric or itaconic acids or anhydrides with vinyl esters, vinyl ethers, vinyl halides, phenylvinyl derivatives, acrylic acid and its esters; these polymers may be esterified. Such polymers are described in particular in U.S. Pat. Nos. 2,047,398, 2,723, 248 and 2,102,113 and GB patent 839 805, and especially those sold under the names Gantrez® AN or ES by the company ISP.

Polymers also falling into this category are the copolymers of maleic, citraconic or itaconic anhydrides and of an allyl or methallyl ester optionally comprising an acrylamide or methacrylamide group, an α-olefin, acrylic or methacrylic esters, acrylic or methacrylic acids or vinylpyrrolidone in their chain, the anhydride functions being monoesterified or monoamidated. These polymers are described, for example, in French patents 2 350 384 and 2 357 241 by the applicant.

E) Polyacrylamides comprising carboxylate groups.

F) Polymers comprising sulfonic groups. These polymers may be polymers comprising vinylsulfonic, styrenesulfonic, naphthalenesulfonic, acrylamidoalkylsulfonic or sulfoisophthalate units.

These polymers may in particular be chosen from:
polyvinylsulfonic acid salts having a molecular weight of between approximately 1000 and 100 000, and also copolymers with an unsaturated comonomer, such as acrylic or methacrylic acids and their esters, and also acrylamide or its derivatives, vinyl ethers and vinylpyrrolidone;
polystyrenesulfonic acid salts, sodium salts, having a molecular weight of approximately 500 000 and of about 100 000. These compounds are described in patent FR 2 198 719;
polyacrylamidesulfonic acid salts such as those mentioned in U.S. Pat. No. 4,128,631.

G) Grafted anionic silicone polymers.

The grafted silicone polymers used are preferably chosen from polymers containing a non-silicone organic backbone grafted with monomers containing a polysiloxane, polymers containing a polysiloxane backbone grafted with non-silicone organic monomers, and mixtures thereof.

H) Anionic polyurethanes, possibly comprising silicone grafts and silicones containing hydrocarbon-based grafts.

By way of examples of fixing polyurethanes, mention may be made, in particular, of the dimethylolpropionic acid/isophorone diisocyanate/neopentyl glycol/polyesterdiol copolymer (also known under the name polyurethane-1, INCI nomenclature) sold under the brand name Luviset® PUR by the company BASF, and the dimethylolpropionic acid/isophorone diisocyanate/neopentyl glycol/polyesterdiol/silicone diamine copolymer (also known under the name polyurethane-6, INCI nomenclature) sold under the brand name Luviset® Si PUR A by the company BASF.

Another anionic polyurethane that may also be used is Avalure UR 450.

It is also possible to use polymers containing sulfoisophthalate groups, such as the polymers AQ55 and AQ48 sold by the company Eastman.

According to the invention, the anionic polymers are preferably chosen from acrylic acid copolymers such as the acrylic acid/ethyl acrylate/N-tert-butylacrylamide terpolymer sold under the name Ultrahold Strong® by the company BASF, and methacrylic acid/ethyl acrylate copolymers, especially in aqueous dispersion, such as Luviflex Soft and Luvimer MAE sold by the company BASF; copolymers derived from crotonic acid such as vinyl acetate/vinyl tert-butylbenzoate/crotonic acid terpolymers and crotonic acid/vinyl acetate/vinyl neododecanoate terpolymers, which are sold under the name Resin 28-2930 by the company Akzo Nobel, polymers derived from maleic, fumaric and/or itaconic acids or anhydrides with vinyl esters, vinyl ethers, vinyl halides, phenylvinyl derivatives, acrylic acid and its esters, such as the monoesterified maleic anhydride/methyl vinyl ether copolymer sold under the name Gantrez® ES 425 by the company ISP, Luviset SI PUR, Mexomere PW, elastomeric or non-elastomeric anionic polyurethanes, and polymers containing sulfoisophthalate groups.

The cationic fixing polymers that may be used according to the present invention are preferably chosen from polymers comprising primary, secondary, tertiary and/or quaternary amine groups forming part of the polymer chain or directly attached thereto, and having a molecular weight of between 500 and approximately 5 000 000 and preferably between 1000 and 3 000 000.

Mention may more particularly be made, among these polymers, of the following cationic polymers:

(1) Homopolymers or copolymers derived from acrylic or methacrylic esters or amides and comprising at least one of the units of following formulae:

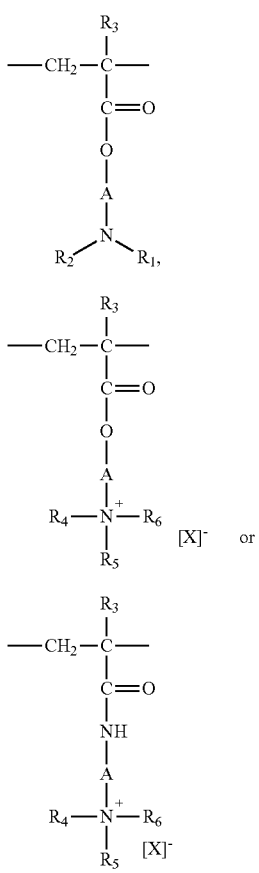

in which:

$R_3$ denotes a hydrogen atom or a $CH_3$ group;

A is a linear or branched alkyl group comprising from 1 to 6 carbon atoms or a hydroxyalkyl group comprising from 1 to 4 carbon atoms;

$R_4$, $R_5$ and $R_6$, which may be identical or different, represent an alkyl group having from 1 to 18 carbon atoms, or a benzyl group;

$R_1$ and $R_2$, which may be identical or different, each represent a hydrogen atom or an alkyl group having from 1 to 6 carbon atoms;

X denotes a methosulfate anion or a halide, such as chloride or bromide.

The copolymers of class (1) further contain one or more units deriving from comonomers which may be chosen from the class of acrylamides, methacrylamides, diacetone acrylamides, acrylamides and methacrylamides substituted on the nitrogen by $C_1$-$C_4$ alkyl groups, groups derived from acrylic or methacrylic acids or esters thereof, vinyllactams such as vinylpyrrolidone or vinylcaprolactam, and vinyl esters.

Thus, among these copolymers of class (1), mention may be made of:

copolymers of acrylamide and of dimethylaminoethyl methacrylate which is quaternized with dimethyl sulfate or with a dimethyl halide, such as that sold under the name Hercofloc® by the company Hercules, copolymers of acrylamide and of methacryloyloxyethyltrimethylammonium chloride, described for example in patent application EP-A-080976 and sold under the name Bina Quat P 100 by the company Ciba Geigy, the copolymer of acrylamide and of methacryloyloxyethyltrimethylammonium methosulfate, such as that sold under the name Reten by the company Hercules, quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755, or alternatively the products known as Copolymer® 845, 958 and 937. These polymers are described in detail in French patents 2 077 143 and 2 393 573, polymers comprising a fatty chain and comprising a vinylpyrrolidone unit, such as the products sold under the names Styleze W20 and Styleze W10 by the company ISP, dimethylaminoethyl methacrylate/vinylcaprolactam/vinylpyrrolidone terpolymers, such as the product sold under the name Gaffix VC 713 by the company ISP, and quaternized vinylpyrrolidone/dimethylaminopropylmethacrylamide copolymers, such as the products sold under the name Gafquat® HS 100 by the company ISP.

(2) Cationic guar gums, preferably containing quaternary ammonium, such as those described in U.S. Pat. Nos. 3,589,578 and 4,031,307, such as guar gums containing trialkylammonium cationic groups. Such products are sold in particular under the trade names Jaguar C13 S, Jaguar C 15 and Jaguar C 17 by the company Meyhall.

(3) Quaternary copolymers of vinylpyrrolidone and of vinylimidazole.

(4) Chitosans or salts thereof; the salts which can be used are in particular the acetate, lactate, glutamate, gluconate or pyrrolidonecarboxylate of chitosan.

Among these compounds, mention may be made of chitosan having a degree of deacetylation of 90.5% by weight, sold under the name Kytan Brut Standard by the company Aber Technologies, and chitosan pyrrolidonecarboxylate sold under the name Kytamer® PC by the company Amerchol.

(5) Cationic cellulose derivatives, such as copolymers of cellulose or of cellulose derivatives grafted with a water-soluble monomer comprising a quaternary ammonium and described in particular in U.S. Pat. No. 4,131,576, such as hydroxyalkylcelluloses, for instance hydroxymethyl-, hydroxyethyl- or hydroxypropylcelluloses, grafted in particular with a methacryloyloxyethyltrimethylammonium, methacrylamidopropyltrimethylammonium or dimethyldiallylammonium salt.

The commercial products corresponding to this definition are more particularly the products sold under the name Celquat L 200 and Celquat H 100 by the company National Starch.

The amphoteric fixing polymers that can be used in accordance with the invention can be chosen from polymers comprising units B and C distributed randomly in the polymer chain, in which B denotes a unit deriving from a monomer comprising at least one basic nitrogen atom and C denotes a unit deriving from an acid monomer comprising one or more carboxylic or sulfonic groups, or alternatively B and C can denote groups deriving from carboxybetaine or sulfobetaine zwitterionic monomers; B and C can also denote a cationic polymer chain comprising primary, secondary, tertiary or quaternary amine groups, in which at least one of the amine groups bears a carboxylic or sulfonic group connected via a hydrocarbon-based group, or alternatively B and C form part of a chain of a polymer containing an ethylenedicarboxylic unit in which one of the carboxylic groups has been made to react with a polyamine comprising one or more primary or secondary amine groups.

The amphoteric polymers corresponding to the definition given above that are more particularly preferred are chosen from the following polymers:

1) Polymers resulting from the copolymerization of a monomer derived from a vinyl compound bearing a carboxylic group, such as, more particularly, acrylic acid, methacrylic acid, maleic acid or α-chloroacrylic acid, and of a basic monomer derived from a substituted vinyl compound containing at least one basic atom, such as, more particularly, dialkylaminoalkyl methacrylate and acrylate, and dialkylaminoalkylmethacrylamide and -acrylamide. Such compounds are described in U.S. Pat. No. 3,836,537.

The vinyl compound may also be a dialkyldiallylammonium salt such as diethyldiallylammonium chloride.

2) Polymers containing units deriving:
a) from at least one monomer chosen from acrylamides or methacrylamides substituted on the nitrogen with an alkyl group,
b) from at least one acidic comonomer comprising one or more reactive carboxylic groups, and
c) from at least one basic comonomer such as acrylic and methacrylic acid esters containing primary, secondary, tertiary and quaternary amine substituents, and the product of quaternization of dimethylaminoethyl methacrylate with dimethyl or diethyl sulfate.

The N-substituted acrylamides or methacrylamides that are more particularly preferred according to the invention are groups in which the alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are more particularly chosen from acrylic acid, methacrylic acid, crotonic acid, itaconic acid, maleic acid and fumaric acid and alkyl monoesters, containing 1 to 4 carbon atoms, of maleic or fumaric acids or anhydrides. The preferred basic comonomers are aminoethyl, butylaminoethyl, N,N'-dimethylaminoethyl and N-(tert-butyl)aminoethyl methacrylates. The copolymers of which the CTFA (4th edition, 1991) name is octylacrylamide/acrylates/butylaminoethyl methacrylate copolymer, such as the products sold under the name Amphomer® or Lovocryl® 47 by the company National Starch, are particularly used.

3) Alkylated and crosslinked polyaminoamides deriving wholly or partly from polyaminoamides of general formula:

(II)

in which $R_4$ represents a divalent group derived from a saturated dicarboxylic acid, from a mono- or dicarboxylic aliphatic acid with an ethylenic double bond, from an ester of an alcohol having 1 to 6 carbon atoms with these acids, or from a group deriving from the addition of any one of said acids with a bis-primary amine or bis-secondary-derived amine, and Z denotes a group of a bis-primary or mono- or bis-secondary polyalkylene-polyamine, and preferably represents:

a) in proportions of from 60 mol % to 100 mol %, the group

(III)

where x=2 and p=2 or 3, or else x=3 and p=2,
this group deriving from diethylenetriamine, triethylenetetramine or dipropylenetriamine;
b) in proportions of from 0 to 40 mol %, the group (III) above, in which x=2 and p=1, which derives from ethylenediamine, or the group deriving from piperazine

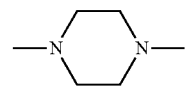

c) in proportions of from 0 to 20 mol %, the —NH(CH2)6-NH— group deriving from hexamethylenediamine, these polyaminoamines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyaminoamide, alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid, 2,4,4-trimethyladipic acid and terephthalic acid, and acids having an ethylenic double bond, such as, for example, acrylic, methacrylic and itaconic acids. The alkane sultones used in the alkylation are preferably propane sultone or butane sultone; the salts of the alkylating agents are preferably the sodium or potassium salts.

4) Polymers containing zwitterionic units of formula:

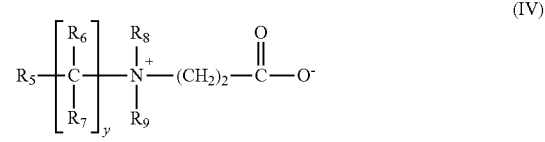

(IV)

in which $R_5$ denotes a polymerizable unsaturated group, such as an acrylate, methacrylate, acrylamide or methacrylamide group, y and z each represent an integer from 1 to 3, $R_6$ and $R_7$ represent a hydrogen atom or a methyl, ethyl or propyl group, $R_8$ and $R_9$ represent a hydrogen atom or an alkyl group such that the sum of the carbon atoms in $R_{10}$ and $R_{11}$ does not exceed 10.

The polymers comprising such units may also comprise units derived from non-zwitterionic monomers such as dimethyl- or diethylaminoethyl acrylate or methacrylate or alkyl acrylates or methacrylates, acrylamides or methacrylamides or vinyl acetate.

5) Polymers derived from chitosan comprising monomer units corresponding to the following formulae:

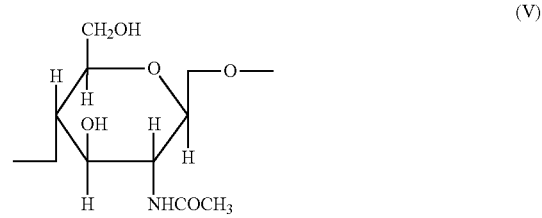

(V)

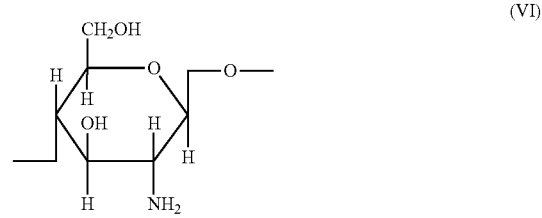

(VI)

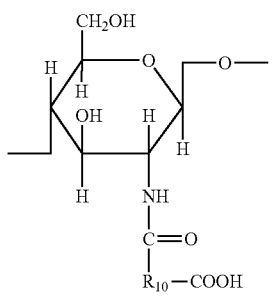

the unit (V) being present in proportions of between 0 and 30%, the unit (VI) in proportions of between 5% and 50% and the unit (VII) in proportions of between 30% and 90%, it being understood that, in this unit F, $R_{10}$ represents a group of formula:

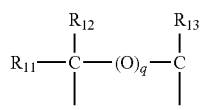

in which, if q=0, $R_{11}$, $R_{12}$ and $R_{13}$, which may be identical or different, each represent a hydrogen atom, a methyl, hydroxyl, acetoxy or amino residue, a monoalkylamine residue or a dialkylamine residue that are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the groups $R_{17}$, $R_{18}$ and $R_{19}$ being, in this case, a hydrogen atom;

or, if q=1, $R_{11}$, $R_{12}$ and $R_{13}$ each represent a hydrogen atom, and also the salts formed by these compounds with bases or acids.

(6) Polymers derived from the N-carboxyalkylation of chitosan.

7) Polymers of units corresponding to general formula (IX), described, for example, in French patent 1 400 366:

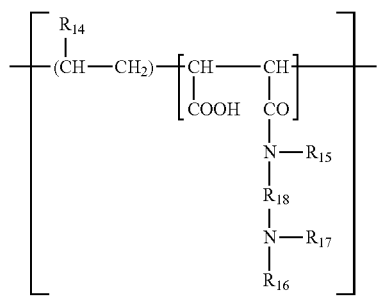

in which $R_{14}$ represents a hydrogen atom or a $CH_3O$, $CH_3CH_2O$, or phenyl group, $R_{15}$ denotes hydrogen or a $C_1$-$C_4$ alkyl group such as methyl and ethyl, $R_{16}$ denotes hydrogen or a $C_1$-$C_4$ alkyl group such as methyl and ethyl, $R_{17}$ denotes a $C_1$-$C_4$ alkyl group such as methyl and ethyl or a group corresponding to the formula: —$R_{18}$—$N(R_{16})_2$, with $R_{18}$ representing a —$CH_2$—$CH_2$—, —$CH_2$—$CH_2$—$CH_2$—, or —$CH_2$—$CH(CH_3)$— group and $R_{16}$ having the meanings given above, and also the higher homologs of these groups, containing up to 6 carbon atoms.

8) Amphoteric polymers of the type -D-X-D-X—, chosen from:

a) polymers obtained by the action of chloroacetic acid or sodium chloroacetate on compounds comprising at least one unit of formula:

$$-D-X-D-X-D- \qquad (X)$$

where D denotes a group

and X denotes the symbol E or E', where E or E', which may be identical or different, denote a divalent group that is an alkylene group with a straight or branched chain containing up to 7 carbon atoms in the main chain, which is unsubstituted or substituted with hydroxyl groups and which can comprise, in addition to oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

$$-D-X-D-X— \qquad (XI)$$

where D denotes a group

and X denotes the symbol E or E' and at least once E'; E having the meaning given above and E' is a divalent group that is an alkylene group with a straight or branched chain having up to 7 carbon atoms in the main chain, which is unsubstituted or substituted with one or more hydroxyl groups and which contains one or more nitrogen atoms, the nitrogen atom being substituted with an alkyl chain that is optionally interrupted by an oxygen atom and necessarily comprises one or more carboxyl functions or one or more hydroxyl functions, betainized by reaction with chloroacetic acid or sodium chloroacetate.

9) Copolymers of ($C_1$-$C_5$)alkyl vinyl ether/maleic anhydride partially modified by semiamidation with an N,N-dialkylaminoalkylamine such as N,N-dimethylaminopropylamine or by semiesterification with an N,N-dialkanolamine. These copolymers may also comprise other vinyl comonomers such as vinylcaprolactam.

According to one preferred embodiment of the invention, the amphoteric fixing polymers that may be used in the aerosol device according to the invention may be chosen from branched block copolymers comprising:

(a) nonionic units derived from at least one monomer chosen from $C_1$-$C_{20}$ alkyl (meth)acrylates, N-mono-($C_2$-$C_{12}$ alkyl)(meth)acrylamides and N,N-di($C_2$-$C_{12}$ alkyl)(meth)acrylamides, (b) anionic units derived from at least one monomer chosen from acrylic acid and methacrylic acid, and (c) polyfunctional units derived from at least one monomer containing at least two polymerizable unsaturated functional groups, and preferably having a structure constituted of hydrophobic blocks onto which are fixed, via polyfunctional units (c), several blocks which are more hydrophilic.

Preferably, the amphoteric polymers have at least two glass transition temperatures (Tg), at least one of which is greater than 20° C. and the other of which is less than 20° C.

The preferred amphoteric polymers are polymers comprising units deriving:

a) from at least one monomer chosen from acrylamides or methacrylamides substituted on the nitrogen with an alkyl group, b) from at least one acidic comonomer comprising one or more reactive carboxylic groups, and c) from at least one basic comonomer such as acrylic and methacrylic acid esters containing primary, secondary, tertiary and quaternary amine substituents, and the product of quaternization of dimethylaminoethyl methacrylate with dimethyl or diethyl sulfate.

Mention may be made in particular of the polymers sold under the name Amphomer by the company National Starch.

The nonionic fixing polymers that may be used according to the present invention are chosen, for example, from:

polyalkyloxazolines, vinyl acetate homopolymers, vinyl acetate copolymers, for instance copolymers of vinyl acetate and of acrylic ester, copolymers of vinyl acetate and of ethylene, or copolymers of vinyl acetate and of maleic ester, for example dibutyl maleate, homopolymers and copolymers of acrylic esters, for instance copolymers of alkyl acrylates and of alkyl methacrylates, such as the products provided by the company Rohm & Haas under the names Primal® AC-261 K and Eudragit® NE 30 D, by the company BASF under the name 8845, or by the company Hoechst under the name Appretan® N9212, copolymers of acrylonitrile and of a nonionic monomer chosen, for example, from butadiene and alkyl (meth)acrylates, such as the products provided under the name CJ 0601 B by the company Rohm & Haas, styrene homopolymers, styrene copolymers, for instance copolymers of styrene and of alkyl (meth)acrylate, such as the products Mowilith® LDM 6911, Mowilith® DM 611 and Mowilith® LDM 6070 provided by the company Hoechst, the products Rhodopas® SD 215 and Rhodopas® DS 910 provided by the company Rhone-Poulenc, copolymers of styrene, of alkyl methacrylate and of alkyl acrylate, copolymers of styrene and of butadiene, or copolymers of styrene, of butadiene and of vinylpyridine, polyamides, vinyllactam homopolymers such as vinylpyrrolidone homopolymers and such as the polyvinylcaprolactam sold under the name Luviskol® Plus by the company BASF, vinyllactam copolymers, such as a poly(vinylpyrrolidone/vinyllactam) copolymer sold under the trade name Luvitec® VPC 55K65W by the company BASF, poly(vinylpyrrolidone/vinyl acetate) copolymers, such as those sold under the name PVPVA® S630L by the company ISP, Luviskol® VA 73, VA 64, VA 55, VA 37 and VA 28 by the company BASF and poly(vinylpyrrolidone/vinyl acetate/vinyl propionate) terpolymers, for instance the product sold under the name Luviskol® VAP 343 by the company BASF, and poly(vinyl alcohols).

The alkyl groups of the nonionic polymers mentioned above preferably have from 1 to 6 carbon atoms.

The fixing polymer is preferably an anionic, amphoteric or nonionic fixing polymer. The fixing polymer is more preferably an anionic or nonionic fixing polymer.

When they are present, the fixing polymer(s) is or are preferably present in an amount ranging from 0.1% to 20% by weight, preferably from 0.5% to 10% by weight, better still from 1% to 8%, relative to the total weight of the composition, when the propellant(s) are present in the composition.

The composition may also comprise one or more styling powder(s) comprising one or more water-insoluble inorganic compound(s).

The term "styling powder" is intended to mean a powder constituted of one or more water-insoluble inorganic compound(s) having a capacity for shaping the head of hair or for the durability of this shaping.

The water-insoluble inorganic compound(s) are chosen from metal carbonates, oxides and sulfates and from silicates containing magnesium.

For the purposes of the present invention, the term "water-insoluble" is intended to mean a compound of which the solubility at spontaneous pH in water at 25° C. and at atmospheric pressure is less than 0.1%.

Examples include more particularly the carbonates, oxides and sulfates of alkaline earth metals such as beryllium, magnesium, calcium, strontium, barium and radium, better still magnesium and calcium; the oxides, sulfates and carbonates of aluminium, gallium and indium; and silicates containing magnesium, more particularly those containing an amount of magnesium of more than 10% by weight (on a dry basis) as expressed in terms of magnesium oxide, such as Li—Mg—Na silicates, for instance Laponite XLG, which is provided by the company Rockwood.

More preference will be given to using calcium carbonate, magnesium carbonate, alumina, barium sulfate and/or magnesium oxide, and better still calcium carbonate such as the calcium carbonate sold under the trade name AH Mikhart 40 by the company Provencale S.A. Preferably, these compounds have a mean particle size of from 20 to 50 µm, as water-insoluble inorganic compound(s).

When they are present, the water-insoluble inorganic compound(s) is or are present in an amount ranging from 0.1% to 30% by weight, even better still from 0.5% to 15% by weight, and even more preferentially from 1% to 10% by weight, relative to the total weight of the composition, when the propellant(s) are present in the composition.

The composition may also comprise one or more $C_2$-$C_4$ monoalcohols.

$C_2$-$C_4$ monoalcohol(s) which can be used in the aerosol device of the invention include, in particular, ethanol or isopropanol, or better still ethanol.

When they are present, the $C_2$-$C_4$ monoalcohol(s) is or are preferably present in an amount ranging from 1% to 70% by weight, even better still from 5% to 60% by weight, and even more preferentially from 10% to 50% by weight, relative to the total weight of the composition, when the propellant(s) are present in the composition.

The composition according to the invention may contain one or more additional organic solvents such as polyols, for instance glycerol, propylene glycol or polyethylene glycols.

It may also contain water.

Preferably, the composition according to the invention contains less than 5% by weight of water relative to the total weight of the composition, when the propellant(s) are present in the composition. Even more preferentially, it does not contain any added water. The composition is then said to be anhydrous.

The container of the device according to the invention also comprises one or more propellants.

Examples of propellant which can be used in the aerosol device of the present invention are liquefied gases such as dimethyl ether, chlorinated and/or fluorinated hydrocarbons such as 1,1-difluoroethane, or volatile hydrocarbons such as, in particular, $C_3$-$C_5$ alkanes, such as propane, isopropane, n-butane, isobutane or pentane, or compressed gases such as air, nitrogen, carbon dioxide, and mixtures thereof.

Mention may be made preferably of dimethyl ether and $C_3$-$C_5$ alkanes and in particular propane, n-butane, isobutane and mixtures thereof.

The agent(s) may be present in the composition or, as a variant, in the container containing the composition, but separate from the composition.

The agent(s) are preferably present in the composition.

When the propellant(s) are present in the composition, it (they) is (are) preferably present in an amount ranging from 10% to 90% by weight, even better still from 15% to 80% by weight and even more preferentially from 20% to 75% by weight relative to the total weight of the composition.

The compositions defined in the invention may further comprise one or more additives chosen from silicones, fatty esters, fatty alcohols, anionic, cationic, nonionic, amphoteric or zwitterionic polymers other than the fixing polymers, fragrances, dyes, UV-protective screening agents, acids, bases, nacres and flakes.

These additives may be present in the composition according to the invention in an amount ranging from 0% to 20% by weight, relative to the total weight of the composition, when the propellant(s) are present in the composition.

Those skilled in the art will take care to choose these optional additives and their amounts so that they do not harm the properties of the compositions of the present invention.

The compositions in accordance with the invention are packaged in an aerosol device comprising a container, also known as a reservoir, and a dispensing means.

The container is pressurized and comprises the composition to be dispensed. The container containing the pressurized composition may be opaque or transparent. It may be made of glass, of polymer or of metal, optionally coated with a protective varnish coat.

As already mentioned previously, the container contains both the propellant(s) and the other ingredients of the composition, in a single compartment, or as a variant in two compartments. According to the latter variant, the container may be constituted of an outer aerosol can comprising an inner bag hermetically welded to a valve. The various ingredients of the composition are introduced into the inner bag and a propellant is introduced between the bag and the can at a sufficient pressure to make the product come out in the form of a spray.

The container is equipped at its top end with a valve that seals the system.

Onto this valve is fitted a dispensing means, on which the user can press to make the product come out. This dispensing means is also known as a diffuser.

As indicated above, the dispensing means according to the invention comprises a body that is open at its two opposite axial ends and an engaging part that is open at its two opposite axial ends, at least partially defining at least one dispensing orifice.

In particular, the dispensing orifice is preferably defined between the body and the engaging part but may, alternatively, be defined entirely by the engaging part.

By virtue of the device of the invention, a passage is formed through the dispensing means and more particularly through the body and the engaging part, allowing a flow of air to be established through the dispensing means when the product to be dispensed is emitted, and this can prove advantageous when the product is emitted in the form of a spray, allowing a current of air to be created through the dispensing means in order to accompany the flow of the spray.

Moreover, the passage through the dispensing means can be produced with dimensions sufficient to allow, if desired, a finger or a lock of hair to be inserted into this passage. This can make it easier to apply a product to the finger or the lock of hair. If desired, the invention can also make it easier to produce a dispensing orifice having an annular cross section between the engaging part and the body, allowing the formation of a hollow spray. Alternatively, a plurality of dispensing orifices are formed between the body and the engaging part, for example in order to dispense the product in the form of a number of sprays or jets. The number of dispensing orifices can in particular be between 2 and 80, limits included, preferably between 5 and 60. It may for example be equal to 10. The dispensing orifices each have for example a cross section greater than or equal to 0.0025 $mm^2$, better still 0.006 $mm^2$ and are preferably spaced apart from one another (measurement along a straight line between the centres of mass of the orifices) by a distance of more than 1 mm.

In another variant, several dispensing orifices are formed entirely in the engaging part. The orifices may be constructed in such a way that the jet exiting from each orifice swirls, especially by virtue of at least two swirl ducts oriented tangentially around the axis of the orifice. The engaging part may have a U-shaped axial half-section. The body may have two concentric mounting skirts between which the engaging part is fastened. The body may comprise a crown into which the engaging part is inserted, the crown possibly bearing one or more reliefs defining, with the engaging part, ducts, especially swirl ducts, for supplying the dispensing orifice.

The body may define a housing that receives the engaging part, which is then called a core.

The dispensing orifice(s) may be open at rest. The expression "at rest" should be understood as meaning before the engaging part is exposed to the pressure of the product to be dispensed. Thus, in this case, the dispensing orifice(s) are already formed and open when the product is sent into the dispensing means in order to be dispensed. Alternatively, the dispensing orifice is formed at the time the product is dispensed, by virtue for example of the elasticity of at least a portion of the body or of the engaging part, which deforms under the pressure of the product at the time it is dispensed.

By virtue of the invention, in the case of spraying, the spray can be emitted at a relatively high flow rate, if desired, while having a dispensing means which has a relatively simple design and functions reliably. In particular, the dispensing orifice may be produced with well-defined dimensions. In addition, the dispensing means may be aesthetically pleasing to the consumer.

The body may have a first surface that flares towards the outside, or converges towards the outside, and the engaging part may have a second surface, opposite the first surface, that diverges towards the outside, or converges towards the outside. The first surface may be conical. The second surface may be conical, with the same angle as the first surface or with a greater or smaller angle.

A different angle that results in a narrowing of the space may lead to an acceleration of the jet before it exits, and this may be advantageous in the context of a spray.

There may be one or more than one dispensing orifice and it may have an annular shape or some other shape. The dispensing orifice may have, in the circumferential direction, a constant width. The one or more dispensing orifices may be defined between two concentric surfaces of revolution, for example in the form of cylinders of revolution.

The dispensing orifice(s) may have axial symmetry, preferably rotational symmetry, in particular around the dispensing axis. The dispensing axis is defined by the general direction in which the product is dispensed by the dispensing means.

When the dispensing means comprises several dispensing orifices, they preferably have the following characteristics.

Their cross section is advantageously a disc.

They are preferably cylindrical in shape or approximately cylindrical in shape.

The depth of each orifice is advantageously between 0.5 and 2 mm. A long length makes it possible to create an individual spray with a reduced cone so as to create a tubular effect with a sizeable number of orifices. A short length allows a very wide individual spray and even further enlarges the application surface of the multi-orifice diffuser.

The sum of the cross sections of the orifices in the ring is preferably chosen to be close to the surface area of the orifice in the nozzle.

With the same valve, it is possible to obtain various types of spray by choosing the number and the cross section of the orifices. Use may, for example, be made of a dispensing means according to the invention equipped with 80 orifices of 0.005 $mm^2$ so as to obtain a gentle mist or a dispensing means according to the invention equipped with 10 orifices of 0.1 $mm^2$ so as to obtain a powerful spray.

The orifices may be distributed in various ways. They may be equidistant on the periphery of the ring, equidistant from one another on a portion of the ring, or distributed in equidistant groups composed of several equidistant orifices.

It is possible to create a ring fully supporting the dispensing orifices which may be cylindrical. In this configuration, it is possible to produce small swirl orifices with a different design from the internal and external rings so as to allow the creation of a ring intended to create the "centre post" function at the rear.

The engaging part is preferably attached, thereby making it, and the body, easier to manufacture. Alternatively, the engaging part is moulded in one piece with the body, in particular in the case of the dispensing of a foam, it then being possible for the dispensing orifice to have a larger cross section than in the case of the spraying of a spray.

The space formed between the body and the engaging part is supplied by at least one supply duct, the section of which is preferably greater than that of the dispensing orifice, thereby making it easier to fill this space before the product emerges through the dispensing orifice.

A product dispensing chamber may advantageously be formed, between the engaging part and the body, upstream of the dispensing orifice. This can make the emission of a homogeneous spray, in particular, easier.

The supply duct for the product may open into this chamber, which preferably has an annular shape. Its width, which corresponds to the gap between the engaging part and the body, is preferably greater than the maximum width of the passage, via which the dispensing chamber communicates with the dispensing orifice.

At least one of the body and the engaging part, preferably the body, may have at least one relief for centring the engaging part in relation to the body, and preferably at least ten, better still at least twenty, and even better still at least forty reliefs. These reliefs may extend as far as the edge of the part in which they are produced so as to generate a multitude of orifices via which jets of product exit, the centring reliefs being oriented in particular parallel to the dispensing axis or obliquely in the same circumferential direction around the axis, and optionally also being able to define, between one another, sectional narrowings that cause the jet of product to be accelerated. This or these reliefs are preferably located set back from the dispensing orifice when it is desired to generate a spray in the form of a single jet. The reliefs can be produced on the body, being for example in the form of axial ribs that are distributed regularly around the entire surface of the body opposite the engaging part.

The centring reliefs may optionally ensure alone that the engaging part is held on the body. Alternatively, the engaging part is fixed to the body somewhere other than in the region of the centring reliefs, it being possible in this case for the centring reliefs to have or not have a function of holding the engaging part on the body.

Preferably, the engaging part is fixed in relation to the body. Alternatively, the engaging part is fixed in an adjustable manner in relation to the body, in order for example to allow the user to adjust the width of the dispensing orifice or to close the latter when not in use, for example by screwing it through a quarter turn, this screwing being accompanied by an axial movement of the engaging part in relation to the body.

The engaging part may be flush with the front end of the body so as to generate a spray with an axis substantially parallel to the axis of the engaging part.

The engaging part may extend axially beyond the front end of the body by an amount between 0.01 and 1 mm, better still between 0.01 and 0.5 mm. The spray may then diverge towards the axis of the engaging part.

The engaging part may be axially set back from the front end of the body by an amount between 0.01 and 1 mm, better still between 0.01 and 0.5 mm. The spray may then converge towards the axis of the engaging part.

The invention makes it possible to easily produce, if desired, a dispensing orifice having a circular internal contour. The inside diameter of the passage formed through the dispensing means is for example greater than or equal to 10 mm, better still greater than or equal to 15 mm, 20 mm or 30 mm. When the passage does not have a circular section, the "inside diameter" denotes the diameter of the largest circle inscribed in this passage.

The dispensing means may comprise at least two housings and two engaging parts that are disposed in the housings and each define with the body, at rest, a dispensing orifice according to the invention. The dispensing axes may then be parallel or not parallel, intersecting or not intersecting, for example may converge towards one another.

The dispensing orifice may have, in axial half-section, an axis that converges or diverges in relation to the spraying direction.

The invention also relates to an aerosol device comprising:
- a container containing:
  - one or more propellants, and
  - a composition comprising one or more fixing polymers and/or one or more styling powder(s) comprising one or more water-insoluble inorganic compounds, it being possible for the propellant(s) to be present in the composition or, in the container, separate from the composition,
- a means for dispensing said composition comprising:
- a body,
- an engaging part, in particular a core, defining with the body, at rest, at least one dispensing orifice having an annular cross section.

The invention also relates to an aerosol device comprising:
- a container comprising a valve rod or pump rod, containing:
  - one or more propellants, and
  - a composition comprising one or more fixing polymers and/or one or more styling powder(s) comprising one or more water-insoluble inorganic compounds, it being possible for the propellant(s) to be present in the composition or, in the container, separate from the composition,
- a means for dispensing said composition comprising:
  - a body provided with an end piece for connecting to the valve rod or pump rod,
  - a part attached to the body, at least partially defining a dispensing orifice having in particular an annular cross section at rest or several dispensing orifices distributed around a dispensing axis (Z),
- the dispensing means not being a through-dispensing means along the dispensing axis (Z),
- the body being closed along the dispensing axis (Z) and said part being in particular of annular shape, or
- the body having a through-opening along the dispensing axis (Z) and said part closing this opening.

BRIEF DESCRIPTION OF THE DRAWINGS

The invention may be better understood from reading the following detailed description of non-limiting illustrative embodiments thereof and from examining the appended drawing, in which:

FIGS. 4A to 4F illustrate various arrangements, among others, of the engaging part and the body, FIGS. 8A and 8B are partial front views of different examples of configurations of the engaging part from FIG. 7, FIGS. 10A and 10B are front views along X of different examples of configurations according to FIG. 9, FIG. 11 is a view similar to FIG. 2 of a variant embodiment of the dispensing means, FIGS. 12A to 12C illustrate various examples of arrangements of the reliefs on the body, FIGS. 13A to 13C illustrate various examples of configurations of the engaging part with respect to the body.

Figure 1:
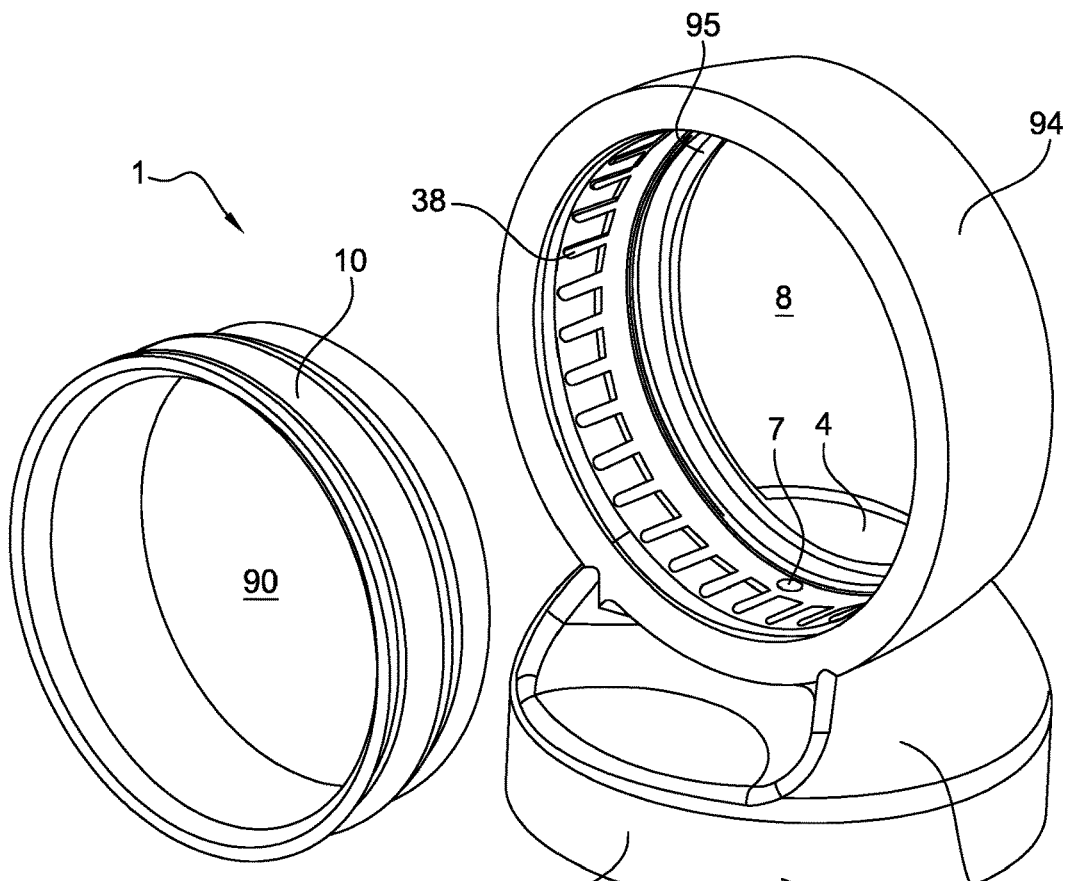
FIG. 1 schematically shows a perspective view of an example of a dispensing means produced in accordance with the invention, before the engaging part is fitted on the body of the dispensing means.

In the drawing, the actual respective proportions of the various constituent elements have not always been respected, for the sake of clarity.

Figure 2:
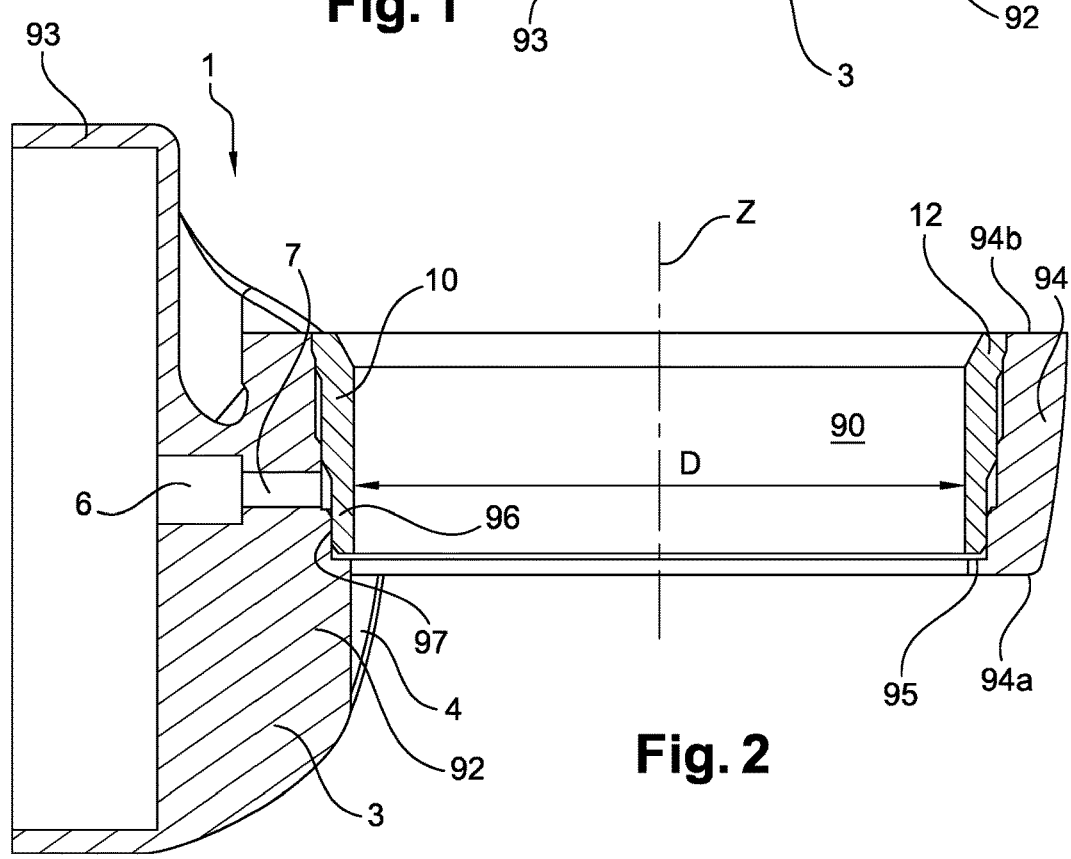
FIG. 2 shows the dispensing means after the engaging part has been fitted in the body.
Figure 3:
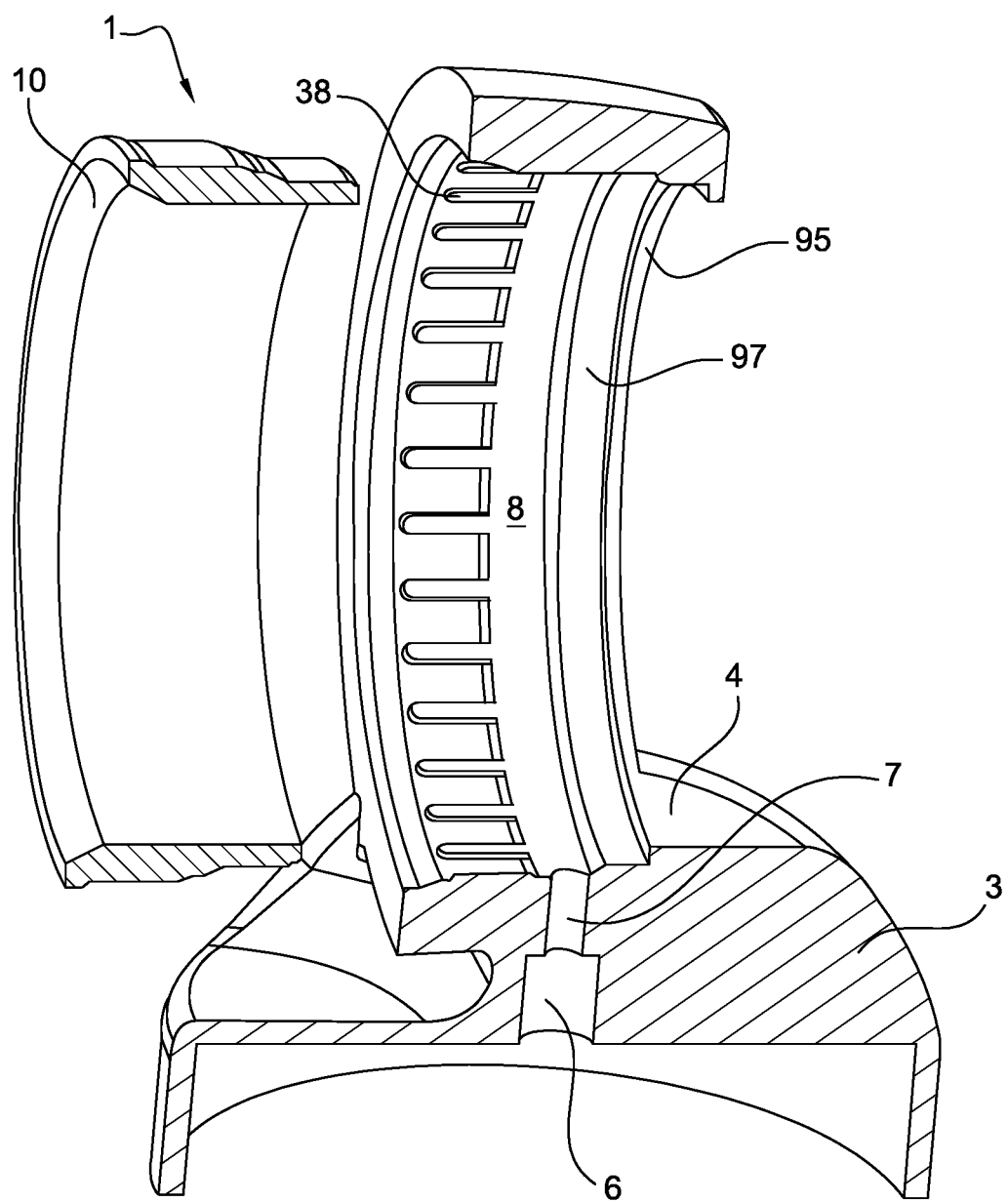
FIG. 3 is a view similar to FIG. 1 in partial section.

The dispensing means 1 shown in FIGS. 1 to 3 is intended to be fitted on a container (not shown) provided with a hollow valve rod or hollow pump rod, through which the product to be dispensed that is contained in the container is conveyed towards the dispensing means 1.

The container may in particular be a pressurized container of the aerosol can type, containing a propellant gas such as compressed air, for example, or a liquefied gas.

The container may be provided with a valve and the valve may be opened for example by pressing the hollow rod or alternatively by tilting the latter. When the container is provided with a pump, the pump may be actuated for example by pressing the hollow rod along its longitudinal axis.

The dispensing means 1 comprises a body 3 which may be produced in an integral manner by moulding a single part or may comprise a plurality of elements produced separately and joined together.

The dispensing means 1 may comprise, as can be seen in FIG. 2, a housing 6 intended to engage with the hollow rod in order to allow the product delivered through the latter to reach a supply duct 7 which opens into a housing 8 in the body 3. The housing 6 has a size adapted to the outside diameter of the rod, so as to obtain a sealed fit of the rod in the housing 6, in order that the product delivered through the rod passes entirely into the supply duct 7. The latter is for example coaxial with the rod of the container but could be oriented in some other way and have for example a plurality of differently oriented portions.

An engaging part 10, called core in the following text when it is inside the body, is fixed in the housing 8 and defines for example with the body 3 a dispensing orifice 12 having an annular cross section, as illustrated.

The expression "annular cross section" should be understood within the meaning of the present invention as meaning any cross section that follows a closed contour, whether this contour is circular, elliptical, polygonal or some other shape.

Passing axially through the core 10 is an opening 90, the inside diameter D of which may be relatively large, for example greater than or equal to 10 mm, better still 15, 20 or 30 mm.

The opening 90 helps to give the dispensing means a particularly aesthetic appearance. In addition, the opening 90 can allow air to flow through the dispensing means under the entrainment effect of a spray emitted through the dispensing orifice 12. This can help to increase the range of the spray and can increase the freshness effect provided thereby, if need be.

The opening 90 may also allow a finger or a lock of hair to be inserted through the dispensing means, and this can make it possible to apply a product in a single movement over the entire circumference of the element inserted through the dispensing means. This can be an advantage for applying for example an antiseptic or care product to a finger or for treating a lock of hair.

The dispensing axis Z may be perpendicular to the longitudinal axis X of the container on which the dispensing means is fitted, as illustrated.

The dispensing means 1 comprises a base 92 which defines a surface 4 on which the user can press in order to bring about dispensing.

The bottom of the base 92 can be extended by an enclosing skirt 93 which covers the upper part of the container.

The housing 8 which receives the core 10 is defined by a crown 94 of axis Z, the lower side of which is joined to the base 92. The supply duct 7 passes through the base 92 and leads into the housing 8 at a distance from the axial ends, along the axis Z, of the crown 94, being preferably closer to the rear end 94a than to the front end 94b, as can be seen in FIG. 2.

The body 3 may have, as illustrated, a shoulder 95 close to the rear end 94a, against which the core 10 can come into axial abutment, if need be, at the end of its fitting.

The core 10 and the housing 8 may have annular surfaces 96 and 97, in sealed contact, in order to close the space formed between the core 10 and the body 3 at the rear of the supply duct 7.

Preferably, the circumferential width I of the dispensing orifice 12, around the spraying direction Z, is constant. If this width I varies, for example so as to take into account the possibly non-uniform pressure drop experienced by the flow of product upstream of the dispensing orifice 12, this does not depart from the scope of the present invention. This non-uniform pressure drop results for example from the geometry of the space between the core and the body, in particular the presence of angles or intersections. By varying the width I, it is possible to ensure that the product can emerge more easily at the point where this pressure drop is greatest, if a spray which is as homogeneous as possible is desired.

The width I of the dispensing orifice is for example between 0.01 and 2 mm.

The core 10 can be fixed to the body 3 in various ways. In the example illustrated in FIGS. 1 to 3, the core 10 is retained on the body 3 by friction.

In the example illustrated, the core 10 is produced separately from the body 3 and is attached to the latter. The core 10 can be produced from the same thermoplastic material as the body 3 or alternatively from a different thermoplastic material. It is also possible to use a metal material to produce the core 10.

Axial ribs 38 are formed on the internal circumference of the housing 8, as can be seen in particular in FIGS. 1 and 3, in order to centre the core 10 in the housing 8. The centring reliefs 38 may be, as illustrated in FIGS. 12A to 12C, parallel or oblique in the circumferential direction with respect to the axis Z, or curved. Each relief 38 may have, when seen in a top view, a contour that is polygonal, in particular rectangular or trapezoidal, or that has a shape that is flared in the direction of the dispensing edge. Two centring reliefs 38 may define, between one another, a narrowing 39 in the vicinity of the dispensing orifice so as to accelerate the fluid via the Venturi effect. The number of centring reliefs 38 is preferably at least 10, better still 20, even better still 40.

Figure 4B:
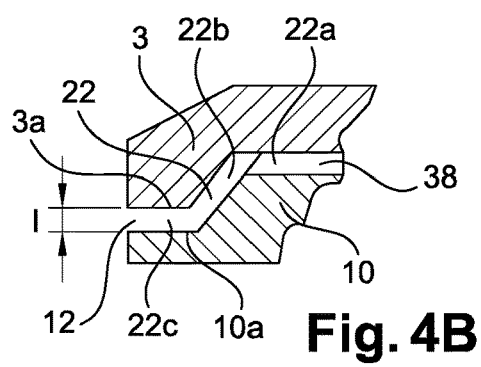
Figure 4C:
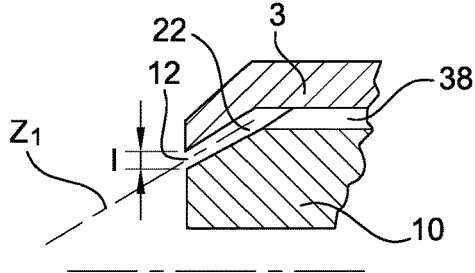
Figure 4A:
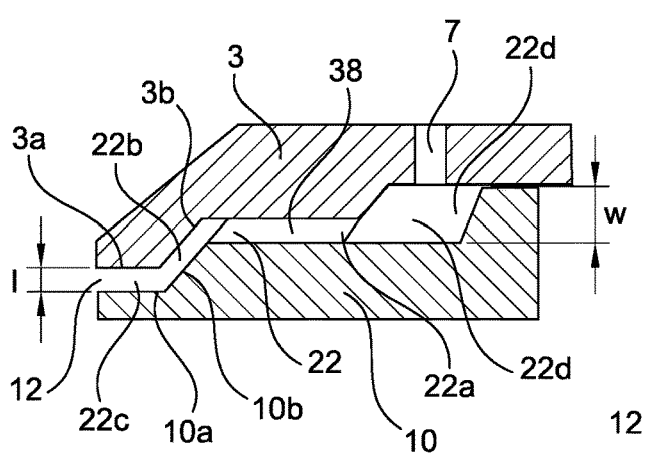

The space 22 formed between the core 10 and the body 3 may have the configuration illustrated schematically in FIG. 4A, and open onto the dispensing orifice 12 by way of an annular terminal portion 22c formed between two surfaces 3a and 10a which are in the form of cylinders of revolution about the axis Z.

The terminal wall 22c is attached to a proximal portion 22a by way of an inclined intermediate portion 22b formed between opposite surfaces 3b and 10b.

The centring reliefs 38 extend in the proximal portion 22a. The latter is supplied with product via the dispensing chamber 22d.

When the user actuates the dispensing means 1, the product passes through the supply duct 7 into the space 22 between the core 10 and the body 3 and can be delivered in the form of a spray through the dispensing orifice 12.

In the example in FIGS. 1 to 3, the spray is continuous angularly around the dispensing axis on account of the absence of contact between the core 10 and the body 3 in the region of the dispensing orifice 12. Specifically, the bearing region or regions between the core 10 and the body 3 are for example located, as illustrated, set back from the dispensing orifice 12 by a distance (measured along the dispensing axis Z) of at least 0.5 mm.

The spray may be discontinuous angularly around the dispensing axis on account of the presence, in particular at the reliefs 38, of contact between the core 10 and the body 3 where the product emerges.

Preferably, the cross section of the supply duct 7 is greater than the section of the dispensing orifice 12 so as to allow the space located upstream of the dispensing orifice to be filled rapidly with the product, this being able to help to form a homogeneous spray right from the start of spraying.

The dispensing chamber 22d formed upstream of the space 22a in which the centring reliefs 38 extend receives the product delivered through the supply duct 7.

The width ω of the dispensing chamber 22d is greater than that I of the terminal portion 22c which opens onto the dispensing orifice 12.

The dispensing chamber 22d improves the dispensing of the product before the latter reaches the narrower portions of the passage through which the product is evacuated.

FIGS. 4B and 4C illustrate different other examples of possible configurations for the space 22 formed between the core 10 and the body 3 for the product to flow to the dispensing orifice.

In the example in FIG. 4B, the space 22 formed between the core and the body comprises a proximal portion 22a in which the reliefs 38 for centring the core 10 in relation to the body 3 extend, extended by an intermediate portion 22b which forms an angle with the spraying direction Z, for example a re-entrant angle. This intermediate portion 22b can be attached to a terminal portion 22c, which opens onto the dispensing orifice 12, this terminal portion being defined for example, as illustrated, between two surfaces 3a and 10a, in the form of cylinders of revolution, parallel to the dispensing direction Z. The variant in FIG. 4B does not have a dispensing chamber.

In the variant in FIG. 4C, the terminal portion 22c communicates directly with that portion 22a in which the centring reliefs 38 extend. The terminal portion 22c forms, for example, an angle with the dispensing direction Z. Thus, in axial half section, the axis Z1 of the orifice 12 is for example convergent, as illustrated.

In the variant in FIG. 4D, the engaging part 10 is outside the body 3. The engaging part 10 is fixed to the body 3 so as to form with the latter the dispensing chamber 22d, facing the supply duct 7. The portions 22a, 22b and 22c allow the product to be conveyed to the dispensing orifice 12.

The supply duct 7 opens for example into the dispensing chamber 22d via a portion oriented parallel to the dispensing axis Z.

Centring reliefs 38 are produced for example on the body 3. The engaging part 10 can be produced, as illustrated, with an annular lip 39 which partially delimits the dispensing chamber 22d and makes it possible to form a narrowing 47 of the section between the chamber 22d and the portion 22a.

FIG. 4E illustrates the possibility of having an angle which is divergent between the axis Z2, in axial half-section, of the orifice 12 and the dispensing axis.

In the variant in FIG. 4F, the possibility of having no angle between the dispensing axis and the axis Z of the engaging part 10 is illustrated. The supply duct 7 opens for example onto a dispensing chamber 22d. The product is conveyed towards the dispensing orifice 12 via ducts 22 comprising the reliefs 38. The reliefs 38 extend as far as the edge of the dispensing orifice 12 and define a plurality of orifices allowing the product to be delivered in the form of a plurality of jets.

The invention is not limited to a dispensing head comprising only one dispensing orifice 12 produced in accordance with the invention.

Figure 5:
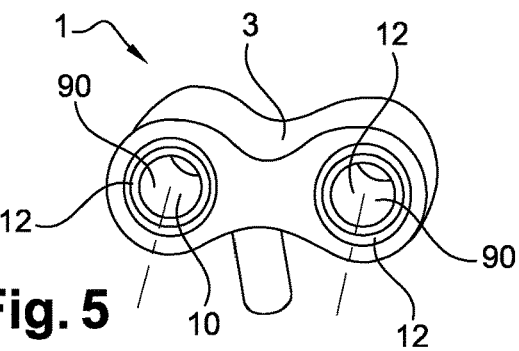
FIG. 5 illustrates the possibility of producing the dispensing means with two dispensing orifices according to the invention.

By way of example, FIG. 5 illustrates a dispensing head 1 which comprises two dispensing orifices 12.

When there are a plurality of dispensing orifices, these may be distributed in multiple ways on the dispensing means. For example, the spraying axes are parallel, or form an angle, in that, for example, they intersect.

Figure 7:
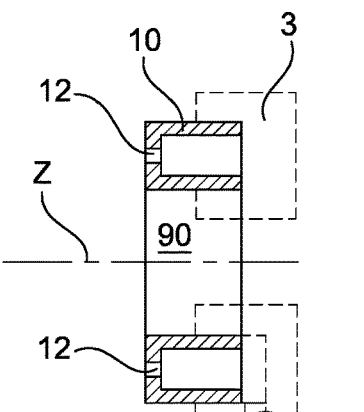
FIG. 7 is an axial section through a variant embodiment of the engaging part.
Figure 8A:
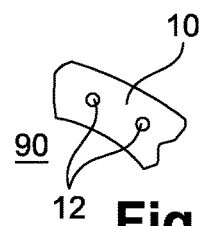

FIGS. 7, 8A and 8B illustrate the possibility for the dispensing means to have a plurality of dispensing orifices 12 formed entirely in the core 10 in order to dispense the product in the form of a plurality of jets for example. The dispensing orifices 12 may have many shapes when observed along their transverse axis, especially being circular or triangular, as illustrated in FIGS. 8A and 8B. The dispensing orifices 12 may be drilled into the core 10, for example by laser drilling.

The core 10 may have a U-shaped axial half-section, as illustrated in FIG. 7. The body 3 may comprise two concentric mounting skirts 41 which define between them a space for mounting the core 10, and may comprise, at its centre, a crown 43 serving to support the engaging part 10. The skirts 41 define, with the crown 43, two annular ducts 45 into which the arms of the U fit. The crown 43 may have, for each orifice 12, two ducts 22 for supplying liquid to this orifice 12.

Figure 14:
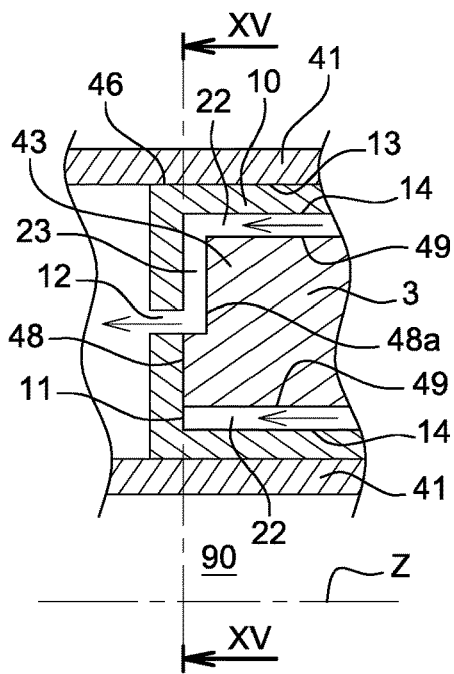
FIG. 14 is a partial axial section through a variant embodiment of the dispensing orifice.
Figure 15:
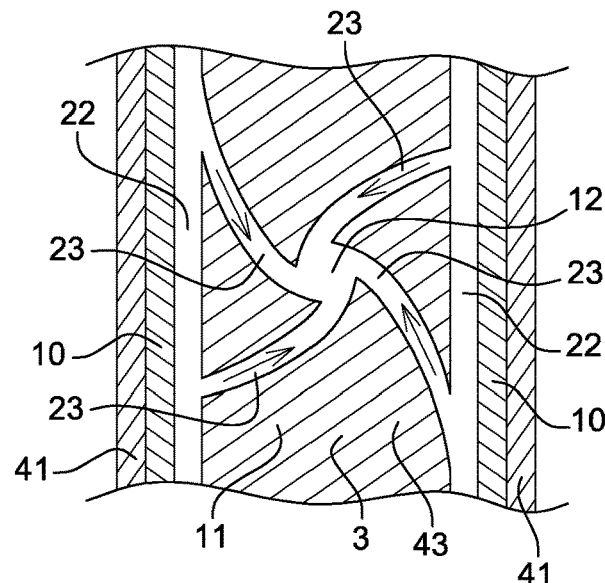
FIG. 15 is a section along XV in FIG. 14.
Figure 16:
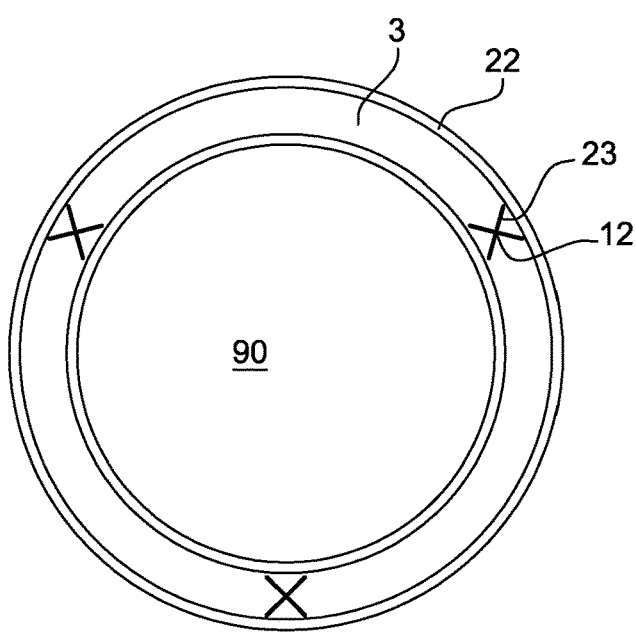
FIG. 16 is an exemplary embodiment of the body according to FIG. 14.
Figure 17:
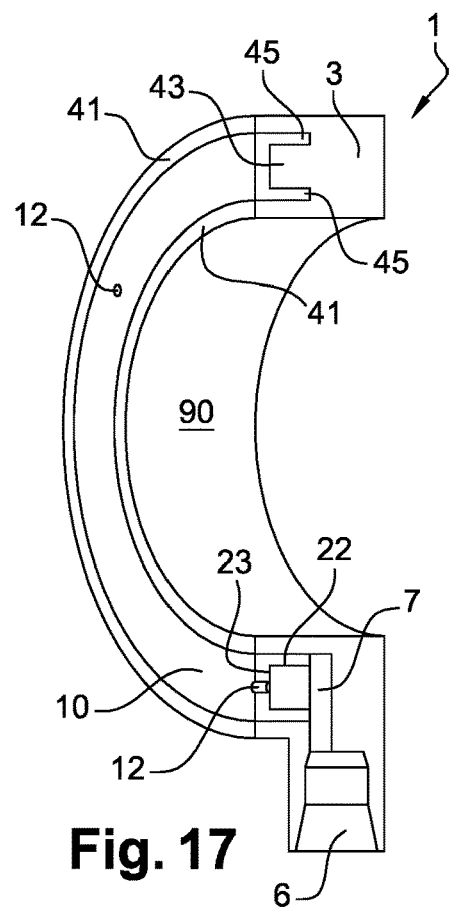
FIG. 17 is a cutaway perspective view of an example of a dispensing means according to the configuration in FIG. 14.

During mounting, as illustrated in FIGS. 14 and 17, the core 10 may bear against the protrusion 43, the end face 48 of the crown 43 being in contact with the internal face 11 of the core 10. The arms of the U of the core 10 are fixed in the ducts 45, the internal face 46 of the mounting skirts 41 being in contact with the face 13 of the core 10. The internal faces 14 of the arms of the U and the lateral surfaces 49 of the crown 43 may define, between one another, the ducts 22 for supplying liquid to the dispensing orifice 12. The crown 43 may have, especially in the form of impressions, on its outer face 48, supply ducts 23 allowing the liquid to pass from the supply ducts 22 to the dispensing orifice 12.

The supply ducts 22 open, upstream of the dispensing orifices 12, onto the supply ducts 23, which lead to the dispensing orifice 12. The supply ducts 23 generate, via their orientation relative to the dispensing orifice, a swirling flow at the outlet of the dispensing orifice 12. This configuration is more particularly useful in the case of a non-liquefied carrier gas.

In one variant, the supply ducts 22 may take the form of impressions on the lateral surface 49 of the body and/or on the internal faces 14 of the core 10.

In one variant (not shown), the core 10 possesses, especially in the form of impressions on its internal face 11, supply ducts 23, the end face 48 of the crown 43 being able to be smooth.

In one variant, the crown 43 is not circumferentially continuous and defines protrusions. The protrusions are placed upstream of the dispensing orifices 12 and may possess, upstream of the dispensing orifices 12, supply ducts 22 and 23 such as described above.

Figure 9:
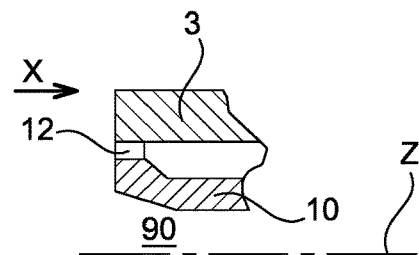
FIG. 9 is a partial axial section through a variant embodiment of the dispensing orifice.
Figure 10A:
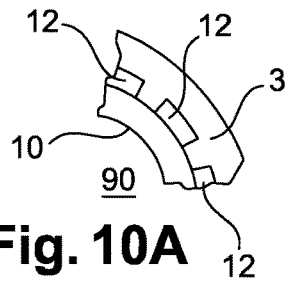

In the variant in FIGS. 4F, 9 and 10, the dispensing orifices 12 are formed between the core 10 and the body 3, being for example distributed all around the spraying axis Z. The core 10 or the body 3 may have centring reliefs 38 that circumferentially bound the dispensing orifices 12. The centring reliefs 38 may, as illustrated in FIGS. 12A to 12C, extend as far as the edge of the core 10 over its entire periphery and define, between one another, dispensing orifices 12. The number of dispensing orifices 12 is preferably at least 10, better still 20, even better still 40. The cross section of a dispensing orifice 12 is for example greater than 0.003 mm$^2$. The dispensing orifices 12 are preferably spaced apart by a space of at least 1 mm, which is the same as the pitch p between the centring reliefs. As illustrated in FIGS. 10A and 10B, the dispensing orifices 12 can have a polygonal cross section, in particular a triangular cross section.

The core 10 may, as illustrated in FIG. 13A, extend set-back relative to the body by an amount between 0.01 and 1 mm, better still between 0.01 and 0.5 mm. The body 3 protrudes into the dispensing orifice and may generate a convergent spray.

The core 10 may, as illustrated in FIG. 13B, be flush with the body 3. The spray can then be straight.

The core 10 may extend, as illustrated in FIG. 13C, forwards relative to the body 3 by an amount between 0 and 1 mm, better still between 0 and 0.5 mm. The spray can then be divergent.

Figure 6:
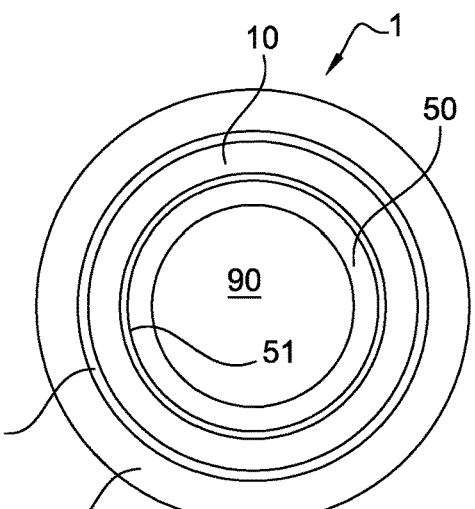
FIG. 6 shows a front view of a dispensing means having concentric dispensing orifices.

If an additional dispensing orifice is provided, for example by attaching inside the core 10 a second core 50 which defines with the first core 10 a second dispensing orifice 51 which is coaxial with the first dispensing orifice, as illustrated in FIG. 6, this does not depart from the scope of the present invention. A passage 90 continues to be formed through the dispensing means.

The dispensing orifice may be supplied with more than one product.

The dispensing means may be supplied with two products which are dispensed through separate dispensing orifices.

It is possible for the axis Z not to be perpendicular to the axis of the rod of the container on which the dispensing means is fitted, as illustrated in FIG. 11. In this example, the axis Z is oriented upward when the container is vertical with the dispensing means at the top.

The supply duct 7 can be oriented substantially parallel to the dispensing axis Z, at least in the case of the portion which opens out facing the engaging part 10. The latter may be produced with an annular lip 39 which defines a narrowing of the section 47.

The configuration may be similar to that in FIG. 4D apart from the fact that the engaging part 10 is outside the body 3 in the example in FIG. 4D and inside it in the example in FIG. 11.

The dispensing means may be arranged so as to allow a protective cap to be fitted and to comprise, if need be, an on/off system that makes it possible to prevent the actuation of the device when the dispensing means is in a certain position with respect to the container or when a locking element of the dispensing means is in a certain position in relation to the latter.

In variants which are not illustrated, the dispensing orifice is formed between a body and an engaging part, the body being radially on the inside with respect to the engaging part, the supply duct for the product passing through the body. All of the features described with reference to the figures can be found in variants in which the body is radially on the inside with respect to the engaging part.

The example that follows serves to illustrate the invention.

EXAMPLE

In the examples that follow, all the amounts are indicated as weight percentage of product as active materials relative to the total weight of the composition.

The following compositions were prepared from the compounds indicated in the table below.

|  | 1 | 2 |
|---|---|---|
| Calcium carbonate (D50 = 35 μm)[1] | 6.00% | — |
| Polyvinylcaprolactam[2] | 2.40% | — |
| Dimethicone and dimethiconol[3] | 0.55 | — |
| Disteardimonium hectorite[4] | 0.50 | — |
| VA/Crotonates/vinyl neodecanoate copolymer[5] | — | 2.80% |
| Aminomethylpropanol | — | 0.29% |
| Xylose | 0.01 | — |
| Fragrance | 0.25% | 0.30% |
| Isobutane | 60.00% | — |
| Dimethyl ether | — | 50.00% |
| Ethanol | qs 100% | qs 100% |

[1]Sold under the trade name Omyacare S 60-AV by Omya,
[2]Sold under the trade name Luviskol Plus by BASF,
[3]Sold under the trade name Mirasil D-DML by Bluestar
[4]Sold under the trade name Bentone 38 VCG by Elementis
[5]Sold under the trade name Resyn 28 - 2930 by Akzo Nobel The aerosol device according to the invention, illustrated in FIG. 1, was used to package the compositions above. It comprises the following characteristics:

Example 1 a valve equipped with a nozzle with an orifice 0.4 mm in size and an internal restriction orifice 0.4 mm in size,
a dispensing means comprising 10 orifices having a unit cross section of 0.25 mm, distributed over the annular surface area.

Example 2 a valve equipped with a nozzle with an orifice 2×0.5 mm in size and an internal restriction orifice 0.8 mm in size, with an additional gas intake 0.4 mm in size,
a dispensing means comprising 10 orifices having a unit cross section of 0.25 mm, distributed over the annular surface area.

The compositions were sprayed onto a head of hair. A wide and vaporous diffusion is obtained which allows an extremely fine and light deposit, uniformly distributed over the head of hair.

After drying, fixing of the hairstyle with a natural look, with no cardboard effect, is noted. The hair is manageable and soft to the touch.

The invention claimed is:

1. An aerosol device comprising:
a container containing:
at least one propellant; and
a composition comprising at least one compound chosen from fixing polymers, styling powders comprising at least one water-insoluble inorganic compound, or mixtures thereof,
wherein the at least one propellant is either present in the composition or in the container, separate from the composition; and
a diffuser for dispensing the composition, the diffuser comprising:
a body extending around a dispensing axis and being open at two opposite axial ends; and
an engaging part extending around the dispensing axis and being open at two opposite axial ends,
wherein the engaging part at least partially defines at least one dispensing orifice.

2. The aerosol device of claim 1, wherein the composition comprises at least one fixing polymer chosen from anionic, amphoteric, or nonionic fixing polymers.

3. The aerosol device of claim 2, wherein the anionic fixing polymers are chosen from copolymers of acrylic and methacrylic acid or salts thereof, copolymers of crotonic acid, polyacrylamides containing carboxylate groups, homopolymers containing sulfonic groups, copolymers containing sulfonic groups, anionic polyurethanes, or anionic grafted silicone polymers.

4. The aerosol device of claim 2, wherein the nonionic fixing polymers are chosen from polyalkyloxazolines, vinyl acetate homopolymers, vinyl acetate copolymers, homopolymers of acrylic esters, copolymers of acrylic esters, copolymers of acrylonitrile and of a nonionic monomer, styrene homopolymers, styrene copolymers, polyamides, vinyllactam homopolymers, vinyllactam copolymers, or polyvinyl alcohols.

5. The aerosol device of claim 1, wherein the at least one propellant is present in the composition, and the composition comprises at least one fixing polymer that is present in an amount ranging from 0.1% to 20% by weight, relative to the total weight of the composition.

6. The aerosol device of claim 1, wherein the composition comprises at least one styling powder comprising at least one water-insoluble inorganic compound, wherein the at least one water-insoluble inorganic compound is chosen from metal carbonates, metal oxides, metal sulfates, or silicates containing magnesium.

7. The aerosol device of claim 6, wherein the at least one water-insoluble inorganic compound is chosen from calcium carbonate, magnesium carbonate, alumina, barium sulfate, magnesium oxide, or mixtures thereof.

8. The aerosol device of claim 1, wherein:
the propellant is present in the composition; and
the composition comprises at least one styling powder comprising at least one water-insoluble inorganic compound, wherein the at least one water-insoluble inorganic compound is present in an amount ranging from 0.1% to 30% by weight, relative to the total weight of the composition.

9. The aerosol device of claim 1, wherein the composition further comprises at least one $C_2$-$C_4$ monoalcohol.

10. The aerosol device of claim 9, wherein the at least one propellant is present in the composition, and the at least one $C_2$-$C_4$ monoalcohol is present in an amount ranging from 1% to 70% by weight, relative to the total weight of the composition.

11. The aerosol device of claim 1, wherein the at least one propellant is chosen from air, nitrogen, carbon dioxide, dimethyl ether, $C_3$-$C_5$ alkanes, n-butane, propane, isobutane, 1,1-difluoroethane, or mixtures thereof.

12. The aerosol device of claim 1, wherein the at least one propellant is present in the composition, and the at least one propellant is present in an amount ranging from 10% to 90% by weight, relative to the total weight of the composition.

13. The aerosol device of claim 1, wherein the at least one dispensing orifice is defined between the engaging part and the body.

14. The aerosol device of claim 1, wherein the at least one dispensing orifice is annular.

15. The aerosol device of claim 14, wherein the at least one dispensing orifice has a constant width in a circumferential direction.

16. The aerosol device of claim 1, wherein the at least one dispensing orifice has axial symmetry.

17. The aerosol device of claim 1, wherein the at least one dispensing orifice comprises a plurality of dispensing orifices.

18. The aerosol device of claim 17, wherein the plurality of dispensing orifices comprises between 2 and 80 dispensing orifices.

19. The aerosol device of claim 17, wherein the plurality of dispensing orifices each have a cross section greater than or equal to 0.0025 $mm^2$.

20. A hair treatment process, comprising:

applying to the hair a composition comprising at least one compound chosen from fixing polymers, styling powders comprising at least one water-insoluble inorganic compound, or mixtures thereof using an aerosol device, wherein the aerosol device comprises:

a container containing the composition and at least one propellant, wherein the at least one propellant is either present in the composition or in the container, separate from the composition; and a diffuser for dispensing the composition, wherein the diffuser comprises:

a body extending around a dispensing axis and being open at two opposite axial ends, and an engaging part extending around the dispensing axis and being open at two opposite axial ends, wherein the engaging part at least partially defines a dispensing orifice.

* * * * *